United States Patent
Evard et al.

(12) 
(10) Patent No.: US 6,616,675 B1
(45) Date of Patent: Sep. 9, 2003

(54) METHODS AND APPARATUS FOR CONNECTING OPENINGS FORMED IN ADJACENT BLOOD VESSELS OR OTHER ANATOMICAL STRUCTURES

(75) Inventors: Philip C. Evard, Palo Alto, CA (US); Joshua Makower, Los Altos, CA (US); J. C. Flaherty, Los Altos, CA (US); Timothy R. Machold, Moss Beach, CA (US); Jason B. Whitt, San Francisco, CA (US); Patrick E. Macaulay, San Jose, CA (US); John T. Garibotto, Palo Alto, CA (US); Alex T. Roth, Redwood City, CA (US)

(73) Assignee: Transvascular, Inc., Menlo Park, CA (US)

( * ) Notice: Subject to any disclaimer, the term of this patent is extended or adjusted under 35 U.S.C. 154(b) by 0 days.

(21) Appl. No.: 09/117,520

(22) PCT Filed: Jan. 31, 1997

(86) PCT No.: PCT/US97/01468
§ 371 (c)(1), (2), (4) Date: Mar. 17, 1999

(87) PCT Pub. No.: WO97/27898
PCT Pub. Date: Aug. 7, 1997

Related U.S. Application Data

(63) Continuation-in-part of application No. 08/730,496, filed on Oct. 11, 1996, now Pat. No. 5,830,222, and a continuation-in-part of application No. 08/730,327, filed on Oct. 11, 1996, now Pat. No. 6,190,353.

(60) Provisional application No. 60/010,614, filed on Feb. 2, 1996.

(51) Int. Cl.[7] ............................................. A61B 17/08

(52) U.S. Cl. .......................................... 606/155; 606/153

(58) Field of Search ............................. 606/1, 108, 194, 606/195, 198, 200, 153–156; 623/1, 12, 1.15, 1.22, 1.2

(56) References Cited

U.S. PATENT DOCUMENTS

| 3,042,021 A | 7/1962 | Read |
| 4,580,568 A | 4/1986 | Gianturco |
| 4,665,918 A | 5/1987 | Garza et al. |

(List continued on next page.)

FOREIGN PATENT DOCUMENTS

| EP | 647438 | 4/1995 |
| RU | 2071732 | 1/1997 |
| WO | 9625886 | 8/1996 |

(List continued on next page.)

OTHER PUBLICATIONS

An Overview of Intravascular Stents: Old and New; Ulrich Sigwart; pp 803–815.

Implantation and Imaging of Coronary Stents; Ruth Haas; pp 233–244.

Nonsuture end–to–end microvascular anastomosis using intravascular stents; C Mikaelsson, E Arnbjornsson; 1996; pp 36–39.

*Primary Examiner*—Michael H. Thaler
(74) *Attorney, Agent, or Firm*—Robert D. Buyan; Stout, Uxa, Buyan & Mullins, LLP

(57) ABSTRACT

Anastomotic connectors and apparatus for forming and/or maintaining connections between openings formed in anatomical structures, such as blood vessels. The apparatus is initially deployed in a first configuration which is sufficiently compact to be delivered through the lumen of a catheter or cannula. Thereafter, the device is expanded to a second configuration whereby it engages the anatomical structures and forms or maintains the desired connection between openings in the anatomical structures.

91 Claims, 8 Drawing Sheets

U.S. PATENT DOCUMENTS

| | | | |
|---|---|---|---|
| 5,035,702 A | | 7/1991 | Taheri |
| 5,035,706 A | | 7/1991 | Giantureo et al. |
| 5,059,166 A | * | 10/1991 | Fischell et al. |
| 5,108,420 A | * | 4/1992 | Marks |
| 5,246,445 A | * | 9/1993 | Yachia et al. |
| 5,269,802 A | * | 12/1993 | Garber |
| 5,282,810 A | | 2/1994 | Allen et al. |
| 5,383,892 A | * | 1/1995 | Cardon et al. ............... 606/198 |
| 5,456,714 A | | 10/1995 | Owen |
| 5,466,242 A | * | 11/1995 | Mori ............................. 623/1 |
| 5,476,506 A | * | 12/1995 | Lunn ........................ 623/1.13 |
| 5,514,176 A | * | 5/1996 | Bosley, Jr. |
| 5,554,162 A | | 9/1996 | DeLange |
| 5,571,167 A | | 11/1996 | Maginot |
| 5,676,670 A | | 10/1997 | Kim |
| 5,683,411 A | | 11/1997 | Kavteladze et al. |
| 5,695,504 A | | 12/1997 | Gifford, III et al. |
| 5,697,971 A | | 12/1997 | Fischell et al. |
| 5,702,419 A | | 12/1997 | Berry et al. |
| 5,713,949 A | | 2/1998 | Jayaraman |
| 5,716,393 A | | 2/1998 | Lindenberg et al. |
| 5,735,892 A | | 4/1998 | Myers et al. |
| 5,735,893 A | | 4/1998 | Lau et al. |
| 5,741,333 A | | 4/1998 | Frid |
| 5,746,766 A | | 5/1998 | Edoga |
| 5,755,769 A | | 5/1998 | Richard et al. |
| 5,755,773 A | | 5/1998 | Evans et al. |
| 5,755,775 A | | 5/1998 | Trerotola et al. |
| 5,776,160 A | | 7/1998 | Pasricha et al. |
| 5,782,844 A | | 7/1998 | Yoon et al. |
| 5,797,920 A | | 8/1998 | Kim |
| 5,817,126 A | | 10/1998 | Imran |
| 5,824,061 A | | 10/1998 | Quijano et al. |
| 5,827,321 A | | 10/1998 | Roubin et al. |
| 5,957,949 A | * | 9/1999 | Leonhardt et al. .......... 606/108 |
| 6,007,544 A | * | 12/1999 | Kim ........................... 606/108 |

FOREIGN PATENT DOCUMENTS

| | | |
|---|---|---|
| WO | 9703616 | 2/1997 |
| WO | 9728745 | 8/1997 |
| WO | 9812989 | 4/1998 |
| WO | 9812990 | 4/1998 |
| WO | 9817204 | 4/1998 |
| WO | 9819607 | 5/1998 |
| WO | 9819629 | 5/1998 |
| WO | 9819630 | 5/1998 |
| WO | 9819632 | 5/1998 |
| WO | 9819634 | 5/1998 |
| WO | 9819636 | 5/1998 |

* cited by examiner

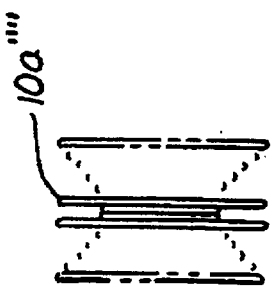
Fig. 2''''
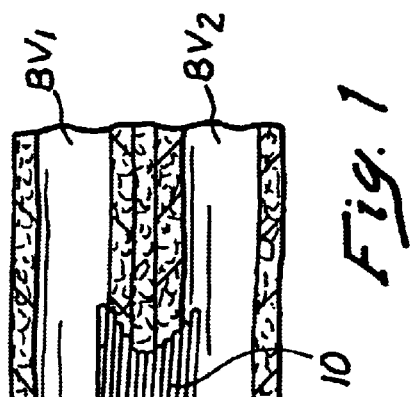
Fig. 1
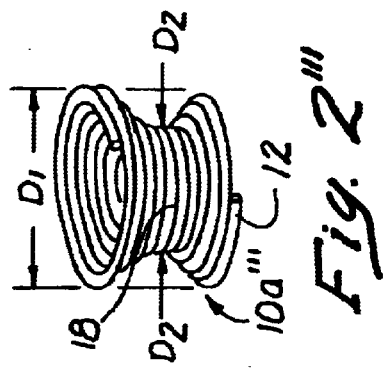
Fig. 2''' 
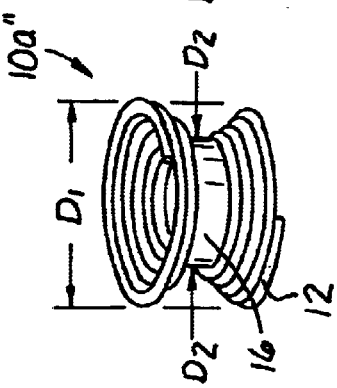
Fig. 2''
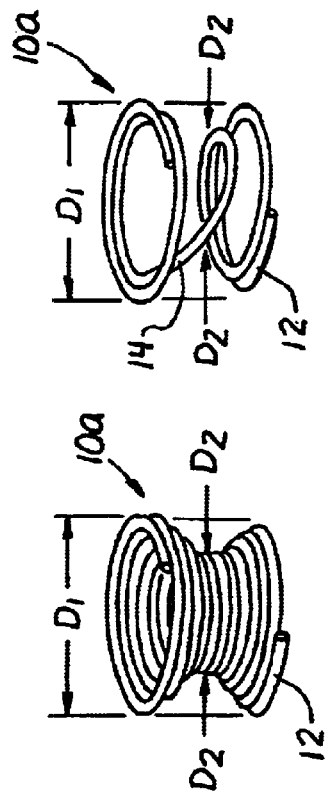
Fig. 2'   Fig. 2

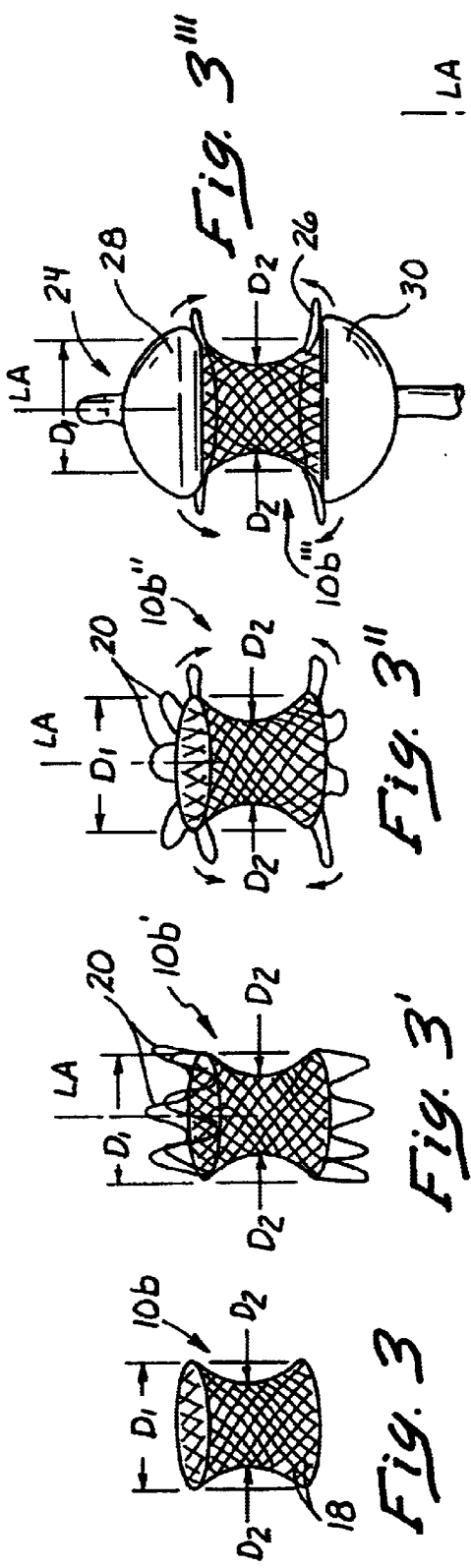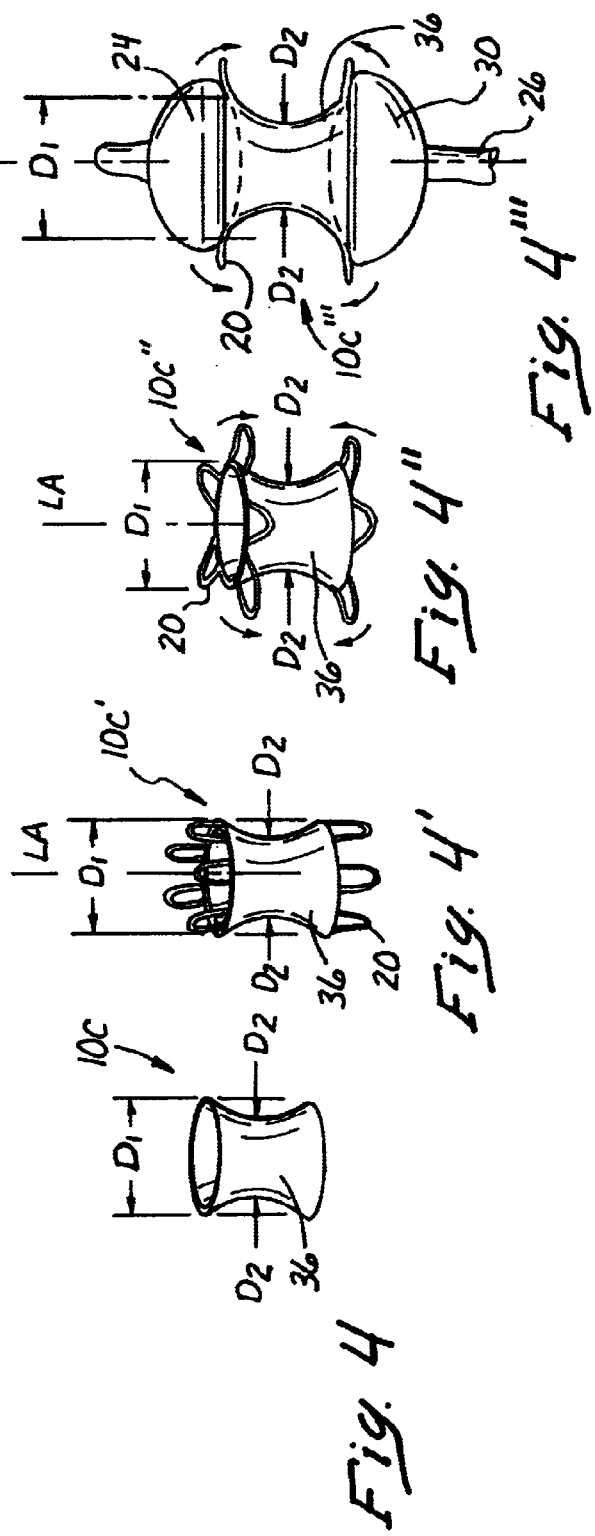

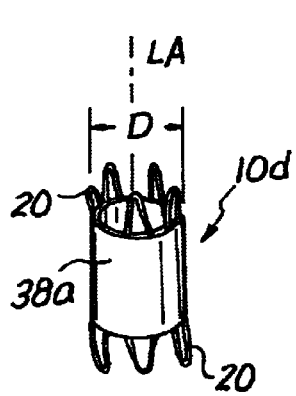
Fig. 5
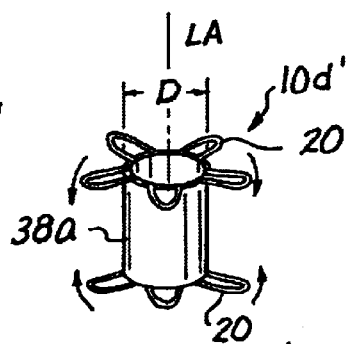
Fig. 5'
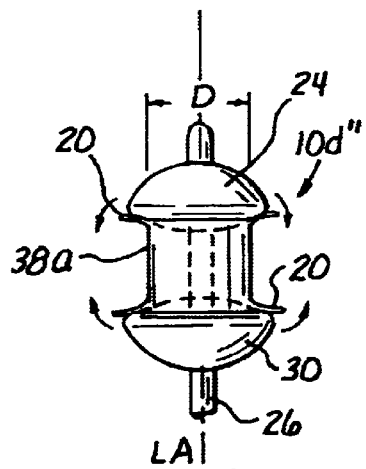
Fig. 5"
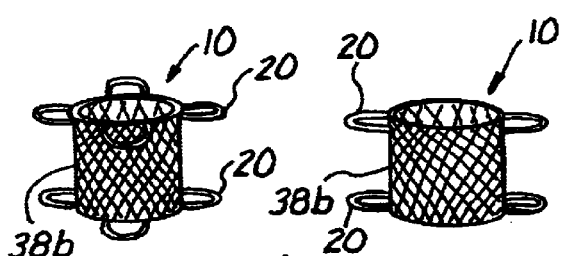
Fig. 5'''     Fig. 5''''     Fig. 5'''''
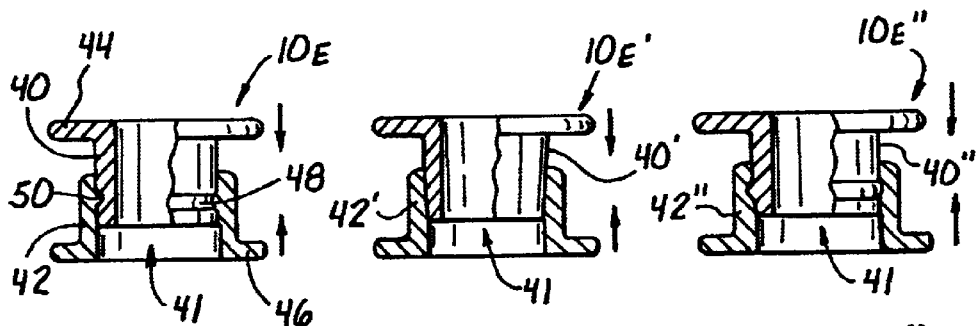
Fig. 6     Fig. 6'     Fig. 6"

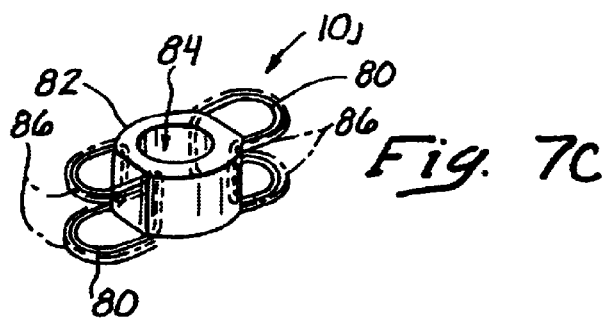
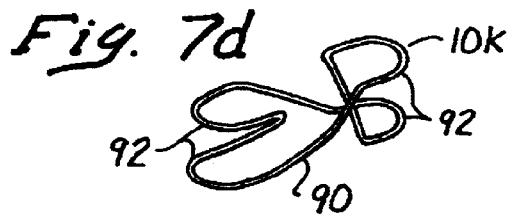
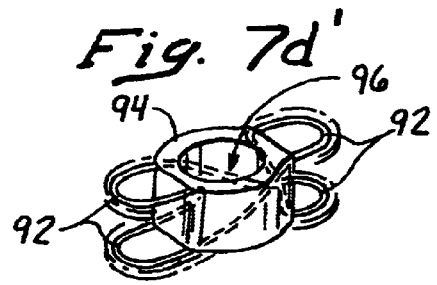
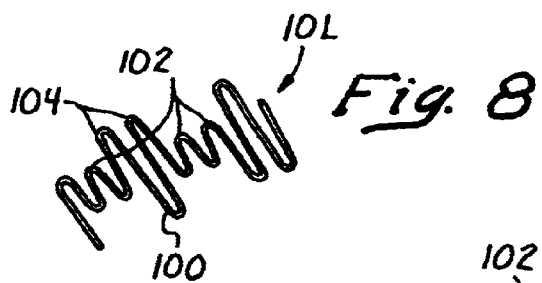
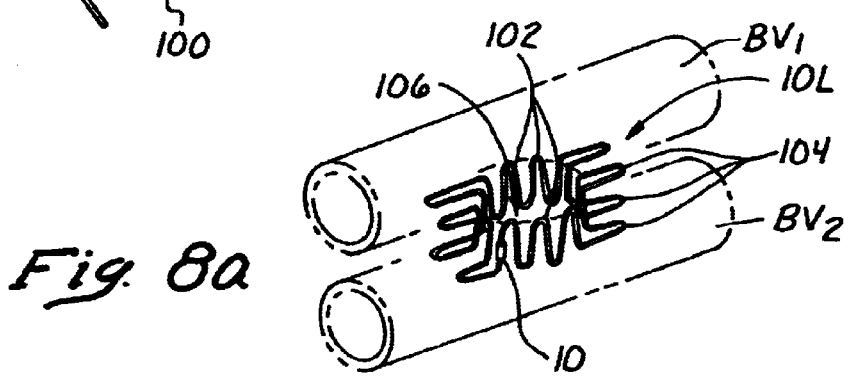

METHODS AND APPARATUS FOR CONNECTING OPENINGS FORMED IN ADJACENT BLOOD VESSELS OR OTHER ANATOMICAL STRUCTURES

RELATED APPLICATIONS

This patent application claims priority to U.S. Provisional Patent Application Ser. No. 60/010,614, filed on Feb. 2, 1996, and is a continuation-in-part of U.S. patent application Ser. No. 08/730,327, filed on Oct. 11, 1996 now U.S. Pat. No. 6,190,353 and Ser. No. 08/730,496, filed on Oct. 11, 1996 now U.S. Pat. No. 5,830,222, the entire disclosure of each such related application being expressly incorporated herein by reference.

FIELD OF THE INVENTION

The present invention relates generally to medical devices, and more particularly to methods and apparatus for making connections between blood vessels or other adjacently situated anatomical or synthetic structures having hollow lumens or cavities formed therein.

BACKGROUND OF THE INVENTION

In modern medical practice, it is often desirable to form connections between adjacent anatomical passageways, or between adjacent segments of a single anatomical passageway. The types of anatomical passageways between which such connections may be made include; blood vessels, vas deferens, fallopian tubes, intestines, lymphatic ducts, grafts, ventricular cavities of the heart or brain, etc.

Recently, applicant has devised certain in situ vascular bypass procedures wherein blood flow passageways (e.g., puncture tracts or interstitial tunnels) are formed between the lumens adjacently situated blood vessels (e.g., between an obstructed coronary artery and an adjacent coronary vein) to bypass a diseased, injured or obstructed segment of one blood vessel. These procedures have previously been described in U.S. patent application Ser. Nos. 08/730,327 and 08/730,496. Also, Provisional U.S. Patent Application Ser. No. 60/010,614 particularly describes certain minimally invasive vascular grafting procedures devised by applicant for by-passing an obstructed artery. In these grafting procedures, a tubular graft (e.g., a segment of an endogenous blood vessel or a tube graft formed of natural or synthetic material) is maneuvered into juxtaposition with the obstructed artery. One or more openings are formed in the graft and the adjacent artery. The openings formed in the graft are then connected to the openings formed in the artery, such that blood may flow between the graft and the artery.

Additionally, various procedures have been reported by others wherein implantable apparatus are used to connect or facilitate flow of bodily fluid between anatomical passageways (e.g., genitourinary ducts). One such procedure is described in U.S. Pat. No. 3,042,021 (Read) entitled BYPASS TYPE INSERT PLUG FOR BODY PASSAGEWAY.

To facilitate the connection of adjacently situated anatomical structures, as in the above-mentioned medical procedures, there exists a need in the art for the design and development of new connector apparatus which may be implanted, through transluminal catheters or probes, to form a secure connection between openings formed in adjacently situated anatomical structures and/or to maintain such openings in direct alignment and/or fluidic communication with each other.

SUMMARY OF THE INVENTION

The present invention provides apparatus for connecting or joining a first opening formed in a first anatomical structure of the type having a hollow inner space or lumen (e.g., a blood vessel, a hollow organ, a chamber of the heart, a vascular graft, etc.) with a second opening formed in a second anatomical structure which also has a hollow innerspace of similar type. In general, these connecting apparatus comprise a) a first engagement member which is engageable with the first anatomical structure, b) a second engagement member which is engageable with the second anatomical structure, and c) a connecting portion which extends or traverses between the first and second engagement members, and serves to hold the openings formed in the first and second anatomical structures in the desired alignment, typically, such that fluid may pass from one anatomical structure into the other.

Further in accordance with the invention, the connecting apparatus may be initially deployable in a radially compact state such that it may be advanced transluminally through the body to a desired implantation site, and is subsequently transitionable to a radially expanded configuration wherein the first engagement member will engage the first anatomical structure and the second engagement member will engage the second anatomical structure. Additionally or alternatively, the first and second engagement members may be initially deployed in non-operative positions (e.g., extending generally parallel to the longitudinal axis of the apparatus) to facilitate transluminal passage and/or placement of the apparatus at the desired implantation site. Thereafter, the first and second engagement members may be transitionable to a second configuration (e.g., an outwardly splayed configuration) such that the first and second engagement members will engage the first and second anatomical structures, as desired. In this manner, the apparatus may be self expanding or self splaying (e.g., formed of resilient or shape memory material) such that the radial expansion or transitioning of the engagement members will occur when surrounding constraint (e.g., constraint of a surrounding catheter wall) has been removed from the apparatus. Alternatively, the apparatus may be plastically deformable and provided with a pressure-exerting tool (e.g., a balloon) which will plastically deform the apparatus to cause the desired radial expansion and/or transitioning of the engagement members after the apparatus has been positioned in its desired implantation site.

Further in accordance with the invention, the engagement members may comprise wire loops, wire members, flanges, extensions, tongues, or any other suitable type of member which will embed into or otherwise engage the adjacent surface of an anatomical structure so as to hold the apparatus at its desired implantation site and/or to maintain the patency of the passageway as well as the length of the connection.

Still further in accordance with the invention, the connecting portion of the apparatus may comprise one or more elongate strands or members, a solid or perforated tube, or any other suitable connecting portion which will serve to link or connect the first and second engagement members and hold them at their desired spaced-apart distance. In some embodiments, the connecting portion may be elastic or biased so as to exert continual pulling force or retraction against the first and second engagement members. In other embodiments, the connecting portion may be rigid and non-elastic so as to remain at a fixed non-alterable length. Additionally, in some embodiments, the connecting portion may define a cylindrical or annular support member which will dilate, support or otherwise maintain any surrounding interstitial tissue in a desired configuration so as to prevent blockage or non-patency of the flow path formed between the first and second openings in the first and second anatomical structures.

Additionally, the connecting portion may be constructed to maintain a minimum passageway diameter between the openings in the first and second anatomical structures. Also, the connecting portion may be constructed to perform some surface modeling or customization of the surrounding tissue as by mechanical pressure exertion, application of a coating or chemical treatment, xenograft, emission of energy, etc. In this manner, the delivery catheter or delivery system used to facilitate implantation of the correct connector apparatus may by equipped with wires, or other energy transmitting members which are in contact with the connector apparatus and which will deliver energy into the connector apparatus, thereby using the connector apparatus as an energy-transferring member for causing deburring, enlargement, scarring, or other modification of the surrounding tissue with which the connector comes in contact. Examples of the types of energy which may be useable for this purpose include electrical energy, radiofrequency, ultrasound, radiation (e.g, beta, gamma, etc.), etc.

Still further in accordance with the invention, the connecting portion of the apparatus may be elastic, adjustable, telescoping, distendible or of accordion construction, etc., so as to adjust or conform to passageways of differing length. This aspect of the invention will allow a connector apparatus to be used for applications wherein the distance between the first and second openings in the first and second anatomical structures may vary and in each specific application, to maintain the first and second anatomical structures in relatively constant tension (i.e., constant force). Alternatively, for connector apparatus which do not incorporate such longitudinal elasticity, adjustability, telescoping, distensible or accordion configuration, the connector apparatus may be provided in a variety of different lengths and the operator may select the appropriate length of the connector apparatus prior to installation.

Still further in accordance with the invention, the leading edge of the apparatus may be a sharpened cutting edge or may be otherwise adapted to cut or sever tissue, such that the delivery and advancement of the apparatus through the openings in the anatomical structures and/or the passageway created therebetween may further serve to form such openings or passageway, or to enlarge, customize, model or otherwise alter the tissue with which it comes in contact.

Still further in accordance with the invention, there are provided connector apparatus having a connecting portion which comprises legs or members which penetrate through tissue surrounding the openings formed in the anatomical structures and/or any intervening tissue located therebetween, such that the connecting portion of the apparatus is embedded within the host tissue and is actually located outside of the channel or passageway formed between the first and second openings in the first and second anatomical structures.

Still further in accordance with invention, there are provided delivery systems and devices for delivering and implanting the connector apparatus of the present invention. These delivery apparatus and devices are typically incorporated into or mounted upon a transluminally advanceable catheter, and comprise a retractable sheath, inflatable balloon, push rod, alter-apposing slider sheaths, or rotatable members which operate to radially expand or advance the connector apparatus into its desired implantation position within the body.

These and other elements and objects of the present invention will be more fully understood and appreciated upon reading of the detailed description of preferred embodiments set forth herebelow, and studying of the accompanying drawings wherein the preferred embodiments are shown.

BRIEF DESCRIPTION OF THE DRAWINGS

FIG. 1 is a partial longitudinal sectional view of two adjacently positioned blood vessels having a blood flow passageway formed therebetween, and a connector apparatus of the present invention implanted within such blood flow passageway to facilitate and maintain the desired side-to-side connection between the blood vessels.

FIG. 2 is a perspective view of a coil-type connector apparatus of the present invention.

FIG. 2' is a perspective view of a modified coil-type connector apparatus of the present invention.

FIG. 2" is a perspective view of another modified coil-type connector apparatus of the present invention having a tubular mid portion.

FIG. 2'" is a perspective view of another coil-type connector apparatus of the present invention having a fused mid-portion.

FIG. 2"" is a side elevtional view of a helical coil connector apparatus of the present invention which is biased to a longitudinally collapsed configuration.

FIG. 3 is a perspective view of a mesh type connector apparatus of the present invention.

FIG. 3' is a perspective view of a mesh type connector apparatus of the present invention having optional engagement members formed on either end thereof.

FIG. 3" is a perspective view of the mesh type connector apparatus of FIG. 3' wherein the engagement members are self-splaying.

FIG. 3'" is a perspective view of the mesh type connector apparatus of FIG. 3' wherein the engagement members are pressure-splayable, and wherein the apparatus is shown in conjunction with a pressure-exerting balloon catheter which is useable to splay the engagement members at the desired implantation site.

FIG. 4 is a perspective view of a tube type connector apparatus of the present invention.

FIG. 4' is a perspective view of a tube type connector apparatus of the present invention having optional engagement members formed on either end thereof.

FIG. 4" is a perspective view of the tube type connector apparatus shown in FIG. 4', wherein the engagement members are self-splaying.

FIG. 4'" is a perspective view of the tube type connector apparatus shown in FIG. 4', wherein the engagement members are pressure-splayable, and wherein the apparatus is shown in conjunction with a pressure-exerting balloon catheter which is useable to cause splaying of the engagement members at the desired implantation site.

FIG. 5 is a perspective view of a cylindrical connector apparatus of the present invention comprising a solid (non-perforated) tube member having optional engagement members formed on either end thereof.

FIG. 5' is a perspective view of a non-hyperbolic, cylindrical connector apparatus wherein the engagement members are self-splaying.

FIG. 5" is a perspective view of a cylindrical connector apparatus wherein engagement members are pressure-splayable, and wherein the apparatus is shown in conjunction with a pressure-exerting balloon-catheter which is usable to cause splaying of the engagement members at the desired implantation site.

FIG. 5''' is a perspective view of a cylindrical connector apparatus wherein the tube member is formed of wire mesh having a multiplicity of openings or perforations formed therein, and multiple engagement members are formed on both ends of the tube member;

FIG. 5"" is a perspective view of a cylindrical connector apparatus wherein the tube member is formed of wire mesh having a multiplicity of openings or perforations formed therein, and two (2) engagement members are formed on each end of the tube member, said engagement members being in direct alignment with one another;

FIG. 5''''' is a perspective view of a cylindrical connector apparatus wherein the tube member is formed of a solid tube, and wherein engagement members comprising semi-circular wire projections are mounted on either end of the tube member;

FIG. 6 is a perspective view of a two-piece rivet-type connector apparatus of the present invention having a first rib-in-groove connection system formed thereon.

FIG. 6' is a perspective view of an alternative two-piece rivet-type connector apparatus of the present invention having a tapered friction-fit engagement system formed thereon.

FIG. 6" is a perspective view of another alternative two-piece rivet-type connector apparatus of the present invention having a second rib-in-groove or magnetic type engagement system formed thereon.

FIG. 7a' is a perspective view of the elastomeric connector apparatus of FIG. 7a.

FIG. 7b' is a perspective view of the connector apparatus shown in FIG. 7b.

FIG. 7c is a perspective view of a connector apparatus of the present invention comprising an elastomeric body having wire support members formed therein.

FIG. 7d is a perspective view of a wire connector apparatus of the present invention.

FIG. 7d' is a perspective view of the wire connector apparatus of FIG. 7d having a cylindrical elastomeric or fabric sleeve formed thereon.

FIG. 7d" is a perspective view of another wire connector apparatus formed of two of the connector apparatus of FIG. 7d, coupled together to form a singular apparatus.

FIG. 8 is a perspective view of a sinusoidal wire connector apparatus of the present invention in a flattened configuration, prior to fabrication into its desired final configuration.

FIG. 8a is a perspective view of the sinusoidal wire connector apparatus of FIG. 8 following fabrication of into its desired final configuration, and showing the apparatus in a preferred implantation position forming a connection between adjacent tubular anatomical conduits.

FIG. 10b is a side elevational view of the pre-notched segment of tubing shown in FIG. 10a.

FIG. 15a' is an exploded view of the connector apparatus shown in FIG. 15a.

DETAILED DESCRIPTION OF THE PREFERRED EMBODIMENTS

Figure 7A:
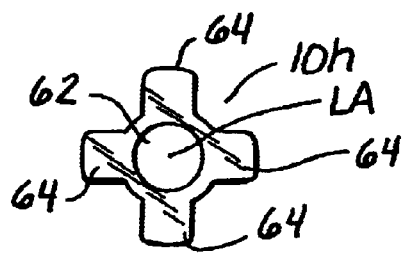
FIG. 7a is a top plan view of a first elastomeric connector apparatus of the present invention comprising a tubular mid-portion having elastomeric engagement members formed at either end thereof.

The following detailed description and the drawings to which it refers are provided for the purpose of describing and illustrating presently preferred embodiments of the invention, and are not intended to limit the scope of the claims in any way.

It is to be understood that each of the structural elements attributes and components shown in the drawings for an embodiment may be incorporated into or combined with any or all of the other embodiments of the invention, so long as such negation may be accomplished without negating the utility or functionality of that embodiment.

Furthermore, it is to be appreciated that no effort has been made to exhaustively describe and illustrate each and every possible embodiment of the invention having each and every possible design or structure feature combineable therewith.

Specifically, the following elements, adaptations or structural attributes may be incorporated into any or all of the embodiments described herein, irrespective of whether such elements, adaptations or attributes are specifically shown in any of the drawings.

1. Radio-opaque construction or radio-opaque markings to enable the connector to be visualized by fluoroscopy, x-ray or Roentgenographic techniques;
2. Non-obstructive or minimally obstructive to flow of fluid through the openings in the anatomical structures between which the connection is formed;
3. Non-thrombogenic or antithrombogenic when used in blood-contacting applications and/or anti-infective or anti-microbial and/or radioactive so as to deter neointimal growth or natural closure or narrowing of the passageway.
4. Capable of withstanding the range of pressures which will be encountered in the intended anatomical application, such as pressures 140–180 mmhg in applications wherein connections between arteries or an artery and vein are formed;
5. Capable of being operatively installed without causing significant necrosis or enhancing or inducing proliferation of tissue surrounding the connector apparatus;
6. Capable of expanding/contracting or otherwise adapting to compliance changes between the connected anatomical structures;
7. The portions of the connector apparatus which abut against or engage the luminal or inner wall of each anatomical structure may be shaped to conform to that luminal or inner wall (e.g., engagement members of flanges may be hemi-cylindrically bowed or cupped to conform to the wall of a blood vessel to which connection is made.
8. The connector apparatus may be structured or designed to maintain a desired cross-sectional dimension or diameter of the openings formed in the adjacent anatomical structures and any interstitial passageway formed between such openings; and
9. The connector apparatus may preferably be formed of a continuous or single structural element having minimal likelihood of breakage or dismemberment after implantation.
10. Capable of incorporating a flow control element or value (e.g., a one-way check valve) to control or maintain a specific pattern or type of flow (e.g., unidirectional flow) through the passageway.
11. The connection portion of the connector apparatus may be adapted to form passageways of various shapes (eg., cylindrical, ovoid, arcuate).
12. Capable of being removed after implantation.
13. The connector apparatus may be constructed with varying amounts of structural support or scaffolding, or may incorporate intraluminally placed structural or non-structural elements which will retard or restrain neointimal growth or natural closure or narrowing of the passageway.
14. The connector apparatus will preferably be capable of withstanding all forces (e.g., hemodynamic pressures, muscular contractions or other forces created by movement or impact of the body) which will be encountered following implantation, without resultant adverse effect (e.g., breakage, dislodgement, slippage, movement or other untoward affect on the connector apparatus).
15. The connector apparatus may be constructed and configured so as to apply residual forces to compress or otherwise minimize the length of the passageway between the first and second anatomical structures following implantation.
16. The connector apparatus may be adapted to receive and transmit energy supplied through the delivery apparatus (e.g., delivery catheter). Such energy may serve to modify the surrounding tissue which defines the openings in the first and second anatomical structures as well as any passageway created between interstitial tissue which resides between the anatomical structures.
17. The connector apparatus may be configured to control or define the geometric shape of the passageway so as to maximize flow performance and/or to minimize adverse flow conditions such as turbulence.
18. The connector apparatus may be constructed to support rotational twisting and torsion without adverse effects.

With reference to the drawings, FIG. 1 provides a general showing of the manner in which the connector apparatus 10 of the present invention is implanted or installed within openings formed in adjacent blood vessels $BV_1$, $BV_2$ to maintain side-by-side connection and direct alignment of the side wall openings formed in the blood vessel $BV_1$, $BV_2$. The blood vessels $BV_1$, $BV_2$ may be endogenous arteries and/or veins in their natural anatomical positions, or may constitute one endogenous artery or vein having a synthetic or biological tube graft placed in juxtaposition thereto.

i. Coil Connectors

FIGS. 2–2''' show several variations of a first embodiment 10a of the connector apparatus of the present invention. Each of the variants shown in FIGS. 2–2''' comprise a helical coil formed of resilient or superelastic wire 12, such coil having opposite ends of a first diameter $D_1$ and a mid-portion of a second diameter $D_2$. The second diameter $D_2$ of the mid-portion of the coil is smaller than the first diameter $D_1$ of the ends, such that the apparatus 10a is generally of all hyperbolic or "hourglass" shape. However, it will be appreciated that other embodiments may also be provided, rather than the hyperbolic or hourglass shape shown in the drawings, the coil is of a cylindrical or frusto-conical shape and is provided with additional engagement members which extend laterally outward from the opposite ends of the coil. The wire 12 of which the apparatus, 10a is formed is sufficiently resilient or superelastic in the range of temperatures in which the apparatus 10a is used (i.e., at room temperature and body temperature) to allow the apparatus 10a to be initially radially compressed (and concurrently longitudinally elongated) into a relatively small diameter, compact configuration which may be inserted into the lumen of a delivery catheter. The delivery catheter is then advanced through the desired anatomical passageway (e.g., blood vessel $BV_1$ or $BV_2$ such that an opening of the catheter is located within the region between the side wall openings in the adjacent anatomical conduits or blood vessels $BV_1$, or $BV_2$. Thereafter, the apparatus 10a is expelled out of the catheter and permitted to resiliently or elastically reassume its hyperbolic or hourglass configuration, such that the ends of the first diameter $D_1$ will engage the walls of each anatomical conduit or blood vessels $BV_1$, $BV_2$ and the mid-portion diameter $D_2$ will reside within the space or tissue tunnel created between the side wall of openings in the adjacent anatomical conduits or blood vessels $BV_1$, $BV_2$.

In the connector apparatus 10a shown in FIG. 2, the entire apparatus 10a is formed of a tightly wound helical wire coil such that each adjacent convolution of the wire 12 is in close juxtaposition or abutment to the adjacent convolution thereof. This provides a hyperbolic coil of substantially continuous construction, as shown in FIG. 2.

FIG. 2' shows a variant of the first embodiment of the connector apparatus 10a wherein the resilient or superelastic wire 12 is tightly wound at either end such that multiple adjacent convolutions of the wire are closely spaced or in direct abutment at either end of the apparatus 10a', while the mid-portion of the apparatus $D_2$ comprises a more loosely wound traversing segment 14 comprising a single strand of the wire 12 which extends from the abutting convolutions at one end of the apparatus 10a' to the abutting convolutions at the other end of the apparatus 10a'.

In the variant shown in FIG. 2", the apparatus 10a" comprises tightly wound helical wire coil segments of generally spiral or frusto-conical configuration located at either end, with a tubular sleeve 16 forming the mid portion of the apparatus 10a". This tubular sleeve 16 may be formed of tubular plastic material such as polytetrafluoroethylene (PTFE), expanded polytetrafluoroethylene (EPTFE) polyethylene (PE), silicone, polyurethane (PU), or polyester. Alternatively, the tubular sleeve 16 may be formed of natural, autologus or xenograft material. The spiral or frusto-conical wire coil segments located at either end of the apparatus 10a" may comprise the opposite ends of a continuous wire coil which extends through the lumen of the tubular sleeve 16, or may comprise two separate, non-continuous coil segments each of which is affixed or mounted to one end of the tubular sleeve 16.

The variant of the connector apparatus 10a''' shown in FIG. 2''' comprises a continuous, tightly wound helical coil of resilient or superelastic wire 12 which is similar in configuration to that shown in FIG. 2, but wherein two or more adjacent convolutions of the wire 12 at the mid-portion of the apparatus 10a''' have been welded, adhered or otherwise fused to one another to form a continuous, tubular mid-portion of diameter $D_2$. Such fusion of the adjacent convolutions of wire 12 forming the mid-portion of the apparatus 10a''' may comprise weldments 18, or adhesive or any other suitable fusion material capable of welding adhering or otherwise fusing the adjacent convolutions of wire 12 to one another.

It will be appreciated that many of the embodiments of the connector apparatus 10 of the present invention may be constructed so as to be biased to a longitudinally shortened or longitudinally collapsed configuration so as to longitudinally compress or confine the tissue between the first and second openings formed in the first and second anatomical structures or blood vessels $BV_1$ $BV_2$. FIG. 2"" shows an example of this concept, as applied to the helical coil connector of FIG. 2. As shown in FIG. 2"", the helical coil connector 10a"", when in its relaxed state, has a longitudinally compact configuration wherein the first and second ends of the coil are close-spaced. When this embodiment of the connector apparatus 10a"" is implanted within the first and second openings formed in the first and second anatomical structures or blood vessels $BV_1$, $BV_2$, the opposite ends of the connector apparatus 10a"" will engage the openings in the adjacent anatomical structures or blood vessels $BV_1$, $BV_2$ and will conform to the length of the channel formed therebetween. In this manner, the resilient nature of the coil will tend to urge or pull the opposite ends of the coil inwardly, thereby longitudinally compressing or constraining the tissues which are located between the opposite ends of the coil. It should be noted, however, that the force exerted by the coil is preferably not to great as to cause undesirable tissue necrosis or undesirable proliferation of tissues which are longitudinally compressed or constrained by this embodiment of the apparatus 10a"". It will be further appreciated that the biasing of the connector apparatus 10a"" to such longitudinally compact configuration will enable the connector apparatus 10a"" to be used in channels or passageways of varying length, thereby eliminating the need for providing manufacturing and stocking a variety of such connector apparatus 10a"" having differing lengths.

ii. Mesh Connectors

FIGS. 3–3''' show several variants of tubular mesh connector apparatus lob having inwardly arched (e.g., hyperboloidal side walls.)

FIG. 3 shows a basic hyperbolic mesh connector apparatus 10b which comprises a tube formed of wire mesh having an inwardly arched, hyperboloidal or "hourglass" configuration. However, it will be appreciated that the wire mesh connectors may alternatively be of cylindrical or frusto-conical configuration with additional engagement members or projections extending laterally outward from the opposite ends of such cylindrical or frusto-conical mesh tube. This embodiment of the connector apparatus 10b has distal ends of a first diameter $D_1$ and a second diameter $D_2$. The diameter $D_2$ of the mid-portion is smaller than the diameters $D_1$ of the ends, thereby providing the desired hyperbolic or hourglass configuration. The mesh structure of the apparatus 10b is preferably formed of a multiplicity of wire segments 18 which are interwoven into the desired mesh structure. The wire segments 18 may be formed of a resilient or superelastic wire material so as to render the apparatus 10b radially compressible (and concurably longitudinally elongatable) to a reduced diameter capable of being positioned within a delivery catheter, and to subsequently allow the apparatus 10b to resiliently self-expand to its desired hyperbolic or hourglass configuration of diameters $D_1$ and $D_2$ after having been expelled from the constraining catheter or other delivery device. In some applications, the hyperbolic or hourglass configuration of the apparatus 10b will be such that the end portions of diameter $D_1$ will engage the walls of the adjacent anatomical passageways or blood vessels $BV_1$, $BV_2$, so as to hold the apparatus 10b in the desired position between the anatomical passageways or blood vessels $BV_1$, $BV_2$. In other embodiments as show, in FIGS. 3', 3", and 3''', one or more splayable engagement members 20 may be formed on one or both ends of the wire mesh tube to facilitate engagement of the opposite ends of the apparatus 10b to the walls of the connected anatomical passageways or blood vessels $BV_1$, $BV_2$.

FIG. 3' shows a variant of the apparatus 10b' having wire loop type engagement members 20 formed on both ends thereof. Initially, as shown in FIG. 3', the wire loop type engagement members 20 will be deployed in extended positions such that they extend longitudinally from either end of the wire mesh tube and are parallel or close to parallel to the longitudinal axis LA of the apparatus 10b'. These engagement members 20 may be formed of resilient or spring material so as to be self splaying (FIG. 3") or may be formed of bendable or malleable material so as to be pressure-splayable (FIG. 3''').

With reference to the particular variant FIG. 3", the resilient or self-splayable engagement members 20 will, when released from the surrounding constraint of the delivery catheter, self-splay (i.e., curve outwardly) to their desired engagement positions wherein such engagement members 20 may be generally perpendicular or near perpendicular to the longitudinal axis LA of the device 10b".

With reference to FIG. 3''', in embodiments wherein the engagement members 20 are formed of plastically deformable or malleable metal or other material which is pressure-deformable, the apparatus 10b''' will be initially positioned within the adjacent openings formed in the first and second anatomical passageways or blood vessels $BV_1$, $BV_2$ such that the engagement members 20 formed on one end of the apparatus 10b''' protrude or extend into the lumen of the first anatomical passageway or blood vessel $BV_1$ and the engagement members 20 on the opposite end of the apparatus 10b''' protrude or extend into the lumen of the second anatomical passageway or blood vessel $BV_2$. A pressure exerting apparatus, such as the dual balloon catheter 24 shown in FIG. 3''', is then utilized to exert, pressure against the engagement members 20 to cause the engagement members to splay or deform outwardly to positions which are substantially perpendicular or near perpendicular to the longitudinal axis LA of the apparatus 10b''', or such that the engagement members will embed or hook into the adjacent tissue of the anatomical structure. In this manner, the engagement members 20 may abut against or enter the adjacent walls of the first and second passageways or blood vessels $BV_1$, or $BV_2$. One type of dual balloon catheter 24 useable for this purpose comprises an elongate pliable catheter 26 having a singular dumbbell-shaped or hour glass shaped balloon or the combination of a first balloon 28 and a second balloon 30 formed at spaced apart location thereon, as shown. The first balloon 28 and second balloon 30 are spaced apart or separated by a distance which is equal to, or bears a predetermined relationship to, the length of the apparatus 10b''' such that the first balloon 28 may be positioned within and adjacent the longitudinally extended engagement members 20 on one end of the apparatus 10b''' and the second balloon 30 may be positioned within and adjacent the longitudinally extended engagement members 20 on the other end of the apparatus 10b'''. Thereafter, the first and second balloons 28, 30 are inflated causing them to exert pressure against the engagement members 20 on both ends of the apparatus 10b''', resulting in the desired splaying or bending of the engagement members 20 to their engagement positions wherein they are generally in apposition to, or embedded in, the wall(s) of the anatomical structure on either side of the channel. Thereafter, the first balloon 28 and second balloon 30 are deflated and the catheter 26 is removed, leaving the connector apparatus 10b''' in its installed and implanted location between the first and second passageways or blood vessels $BV_1$, $BV_2$.

iii. Tube Connectors

FIGS. 4–4''' show several variants of a tube connector apparatus 10c 10c''' which generally comprises a segment of radially compressible or collapsible resilient tube member 30 having inwardly arched, hyperboloidal or "hourglass" shaped side walls having opposite ends of a first diameter $D_1$ and a mid-portion of a second diameter $D_2$. It will be appreciated, however, that the tube may alternatively be of cylindrical or frusto-conical shape with additional engagement members which extend laterally outward from either end of the tube, which may not require expansion for placement.

Specifically, FIG. 4 shows a connector apparatus 10c which comprises a hyperbolic or hourglass shaped tube member 36 which is positionable within side openings formed in two adjacent anatomical passageways (e.g., blood vessels $BV_1$, $BV_2$) such that one end of the tube member 36 having diameter $D_1$ will engage the luminal surface of one of the passageways or blood vessels $BV_1$ and the other end of the tube member 36 also of diameter $D_1$ will engage the luminal surface of the other passageway of blood vessel $BV_2$. The outwardly tapered or enlarged diameters of the ends of the tube members thus serve to engage the anatomical passageways or blood vessels $BV_1$, $BV_2$ without the need for additional flanges, projections or other engagement members on either end of the tube member 36.

FIG. 4' shows the hyperbolic tube member 36 of FIG. 4 with optional engagement members 20 formed on both ends thereof. These engagement members 20 may comprise flanges, tabs, or, as shown, splayable wire loops. These engagement members 20 are initially disposed such that they extend longitudinally from either end of the hyperbolic tube member 36 and are parallel or close to parallel to the longitudinal axis LA of the tube member 36. After the tube member 36 has been placed in its desired position between the two anatomical passageways or blood vessels $BV_1$, $BV_2$, the engagement members 20 are caused to splay outwardly such that they become perpendicular or close to perpendicular to the longitudinal axis LA of the tube member 36, as shown in FIGS. 4'' and 4'''. The engagement members 20 may be formed of resilient, superelastic, shape memory or spring material so as to be self-splayable (FIG. 4'') or may be formed of bendable or plastically deformable material so as to be pressure-splayable (FIG. 4''').

With reference to FIG. 4'', a self-splayable embodiment of the apparatus 10c comprises engagement members 20 which, when relieved of the surrounding constraint of a delivery catheter or other delivery apparatus, will self-splay to their outwardly deployed positions wherein they are generally perpendicular or close to perpendicular to the longitudinal axis LA of the apparatus 10c''.

With reference to FIG. 4''', there is shown an embodiment of the apparatus 10c''' wherein the engagement members 20 are pressure-splayable. This embodiment of the apparatus 10c''' is initially positioned such that the engagement members 20 on one end of the apparatus 10c''' extend into the lumen of one anatomical passageway or blood vessel $BV_1$, and the engagement members 20 on the other end of the apparatus 10c''' extend into the lumen of the second anatomical passageway or blood vessel $BV_2$. A pressure exerting apparatus, such as the above-described balloon catheter 26 having first and second balloons 28, 30, is then utilized to exert pressure upon the engagement members 20 to cause the engagement members to move from their longitudinally extended positions (FIG. 4') to their outwardly splayed (i.e., operative positions wherein they are generally perpendicular or close to perpendicular to the longitudinal axis LA of the apparatus 10c'''. Thereafter, the balloons 28, 30 of the balloon catheter 26 or other pressure-exerting elements of any suitable pressure-exerting tool are deflated or otherwise disengaged and the catheter 26 is removed, thereby leaving the apparatus 10c in its desired position between the first and second anatomical passageways or blood vessels $BV_1$, $BV_2$, with the engagement members 20 in direct abutment with the lumen surfaces of the respective first and second passageways or blood vessels $BV_1$, $BV_2$.

iv. Cylindrical Connectors with Engagement Surface

FIGS. 5–5' show several variants of a cylindrical connector apparatus 10b of the present invention. This cylindrical connector apparatus 10b generally comprises a cylindrical, tubular mid-portion 38 of substantially constant diameter, in combination with one or more engagement members formed on either end thereof. The engagement members 20 may comprise splayable wire loops as shown in the drawings, or any other suitable type of flange, lip, tab or other member capable of abutting against the luminal wall of an anatomical passageway or blood vessel $BV_1$, $BV_2$ to prevent longitudinal slippage or movement of the tubular mid-portion in at least one direction. In this manner, the formation and deployment of such engagement member on either end of the tubular mid-portion 38 will anchor and hold the tubular mid-portion 38 in its desired implantation position between the openings formed in the adjacent passageways of blood vessels $BV_1$ and $BV_2$.

The tubular mid-portion 38 of the apparatus 10*d* may comprise a tube of resilient plastic, woven dacron or any other suitable material which is collapsible to a small diameter so as to be initially packed within the lumen of a delivery catheter, and which is subsequently radially expandable or unfoldable to a desired diameter D such that blood or other bodily fluid may flow through the cylindrical tubular member 38 from one anatomical passageway or blood vessel $BV_1$ into another anatomical passageway or blood vessel $BV_2$. Alternatively, it will be appreciated that the tubular mid-portion 38 may be a rigid or semi-rigid tube formed of metal, carbon or alloy which is generally not radially expandable, but which is provided with additional engagement members which may be splayed or extended from opposite ends of the tubular mid-portion 38 to engage or embed within the adjacent tissue of the anatomical structure. These rigid or semi-rigid tubular mid-portions 38 may be of any suitable shaped configuration, including cylindrical, frusto-conical or hyperbolic (e.g., hourglass) shape.

The engagement members 20 are preferably initially disposed in positions wherein they are longitudinally extended from either end of the cylindrical tubular mid-portion 38 generally parallel or close to parallel to the longitudinal axis LA of the apparatus 10*d* as shown in FIG. 5. The engagement members 20 may be formed of resilient, superelastic, shape memory or spring material so as to be self-splayable (FIG. 5) or may be formed of bendable or plastically deformable material so as to be pressure-splayable (FIG. 5") With reference to FIG. 5', a self-splayable embodiment of apparatus 10*d* comprises engagement members 20 which, when relieved of the surrounding constraint of the delivery catheter or other delivery apparatus, will self-splay to their outwardly deployed position wherein they are generally perpendicular or close to perpendicular to the longitudinal axis LA of the apparatus 10*b'*.

With reference to FIG. 5", in embodiments of the apparatus 10*b"* wherein the engagement members 20 are pressure-splayable. This embodiment of the apparatus 10*b"* is initially positioned such that the engagement members 20 on one end of the apparatus 10*b"* extend into the lumen of one anatomical passageway or blood vessel $BV_1$ and the engagement members 20 on the other end of the apparatus 10*b"* extend into the lumen of the second anatomical passageway or blood vessel $BV_2$. A pressure exerting apparatus, such as the above-described balloon catheter 26 having first and second balloons 28, 30, is then utilized to exert pressure upon the engagement members 20 to cause the engagement members to move from their longitudinally extended positions (FIG. 5) to their outwardly splayed (i.e., operative) positions wherein they are generally perpendicular or close to perpendicular to the longitudinal axis LA of the apparatus 10*d"* (FIG. 5"). Thereafter, the balloons 28, 30 of the balloon catheter 26 or other pressure-exerting elements of any suitable pressure-exerting tool are deflated or otherwise disengaged and the catheter 26 is removed, thereby leaving the apparatus 10*d"* in its desired position between the first and second anatomical passageways or blood vessels $BV_1$, $BV_2$ with the engagement members 20 in direct abutment with the respective first and second passageways or blood vessels $BV_1$, $BV_2$.

v. Rivet Type Connector Apparatus

FIGS. 6–6" show several variants of rivet type connector apparatus which comprise a first tubular member 40 having a first engagement flange 44 formed thereon and a second tubular member 42 having a second engagement flange 46 formed thereon. The first and second tubular members 40, 42 are connectible to one another such the lumens of the tubular members 40, 42 are in direct alignment thereby forming a singular lumen 41 through the center of the apparatus 10*e*, 10*e'*, 10*e"*.

Various snap-fitting or frictional engagement systems may be utilized to securely connect the first and second tubular members 40, 42 to one another, and examples of such snap-fitting or frictional engagement systems are shown in the showings of FIGS. 6, 6' and 6".

With specific reference to FIG. 6, there is provided an annular groove 48 in the outer surface of the first tubular member 40 and a corresponding raised ridge 50 in the outer surface of the second tubular member 42. The raised ridge 50 is sized and configured to snap fit and seat within the groove 48 as the first tubular member 40 is advanced into the interior of the second tubular member 42. When the annular ridge 50 is seated within the corresponding groove, the respective engagements 44, 46 will be held in fixed spaced-apart relation to one another such that the distance between flanges 44, 46 will result in engagement of the flanges with the respective luminal walls of the anatomical passageways or blood vessels $BV_1$, $BV_2$ which are intended to be connected by the apparatus 10*e*.

FIG. 6' shows another connector apparatus 10*e* comprising a first tubular member 40' and a second tubular member 42'. Engagement flanges 44', 46' are formed about the outer ends of the first and second tubular members 40', 42', respectively. When the non-flanged end of the first tubular member 40' is advanced into the non-flanged end of the second tubular member 42', the respective lumens of the two tubular members 40', 42' will be in direct alignment so as to form a single continuous lumen 41 through the center of the apparatus 10*e'*. The outer surface of the first tubular member 40 is tapered inwardly toward the non-flanged end such that, as it is advanced into the interior of the second tubular member 42', the outer surface of the first tubular member 40' will tighten against and frictionally engage the inner surface of the second tubular member 42', thereby holding the first and second tubular members 40', 42' in fixed, connected relation to one another such that the engagement flanges, 44', 46' are held in spaced-apart relation such that the distance there between will cause the flanges 44', 46' to be in abutting contact with the respective luminal surfaces of the first and second passageways or blood vessels $BV_1$, $BV_2$.

vi. Elastomeric Connector Apparatus

FIGS. 7*a*–7*d'* show examples of connector apparatus 10*h*, 10*i* of the present invention formed of elastomeric materials such as a resilient elastomeric polymer (e.g., polyurethane, silicone, etc.).

In particular, FIGS. 7*a*, 7*a'* show an embodiment of a connector apparatus 10*h* comprising an elastomeric, cylindrical tube 60 having a hollow lumen 62 extending longitudinally therethrough and four engagement members in the nature of tabs formed on opposite ends of the tube 60 and extending outwardly therefrom in directions which are substantially perpendicular to the longitudinal axis LA of the tube 60.

Figure 7B:
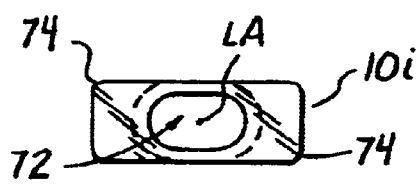
FIG. 7b is a top plan view of another elastomeric connector apparatus of the present invention comprising a tubular mid portion having a non-circular lumen and engagement flanges formed at either end thereof.
Figure 7A:
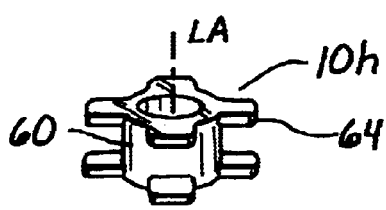
Figure 7B:
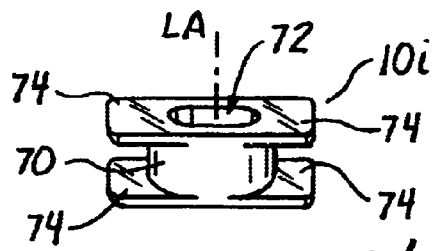

FIGS. 7*b*, 7*b'* show another embodiment of a connector apparatus 10*i* which comprises an ovoid tube member 70 formed of elastomeric material and substantially rectangular engagement members 74 in the nature of flanges formed on either end thereof. The engagement members 74 extend in directions which are parallel to the length-wise axis of the ovoid lumen 72 of the ovoid tube member 70, as shown. The provision of the ovoid tube member 70 having the ovoid lumen 72, and the corresponding configuration and directional orientation of the engagement members 74 will enable this embodiment of the connector apparatus 10i to be utilized in blood vessels or anatomical passageways of relatively small diameter, with openings which are elongate or ovoid so as to permit a greater amount of body fluid to flow through the openings than would be possible than if the openings were of a circular configuration. This is due to the fact that the maximum diameter of any circular opening formed in the side wall of a passageway or blood vessel $BV_1$, $BV_2$ cannot exceed the diameter of the passageway or blood vessel $BV_1$, $BV_2$, while elongate or ovoid openings may have a width which is equal to or slightly less than the diameter of the passageway or blood vessel $BV_1$, $BV_2$ and a length which is larger than the diameter of such passageway or blood vessel $BV_1$, $BV_2$. This tube member 70 may also incorporate any suitable reinforcing material, such as wire. This ovoid or non-circular configuration of the tube member 70 and its lumen 72 may be incorporated into any of the embodiments of the invention described herein, and is not necessarily limited to the particular elastomeric embodiment shown in FIGS. 7b, 7b'.

In each of these elastomeric embodiments shown in FIGS. 7a, 7a', 7b, 7b', the material of which the apparatus 10h, 10i is formed is sufficiently resilient and compressible to be initially packed into the lumen of a delivery catheter, and is sufficiently resilient such that when the apparatus 10h, 10i is expelled or otherwise passed out of the delivery catheter, the absence of restraint upon the apparatus 10h, 10i will allow the apparatus to assume its fully expanded and operative configuration as shown in the figures. When in such fully expanded and operative configuration, the abutment members 64 or 74 will abut against the lumenal surfaces of the passageways or blood vessels $BV_1$, $BV_2$, in the regions immediately surrounding the openings formed therein, and the tube members 60, 70 of the apparatus 10h, 10i will extend between the respective passageways or blood vessels $BV_1$, $BV_2$, thereby forming a conduit or passageway between the openings formed in the passageways or blood vessels $BV_1$, $BV_2$.

vii. Wire Connector Apparatus with Optional Covering

FIGS. 7c–7d' show examples of wire connector members with optional coverings formed thereon. These coverings may cover all or any portion of the apparatus. For example, such covering may be formed on the connecting portion or mid-portion of the apparatus so as to form a sleeve or covering which lines the passageway, while the engagement portions (e.g., extendable engagement members) of the apparatus may remain devoid of such covering. Such coverings may be formed of any suitable material including, but not limited to, elastomeric material, fabrics (e.g., woven polyester) or natural materials such as autologus or xenograft material.

With specific reference to the embodiment shown in FIG. 7c, there are provided two separate generally U-shaped wire members 80 which are partially embedded with an elastomeric tube member 82 having a hollow lumen 84 extending longitudinally therethrough. Optionally, the portions of the wire members 80 which protrude out of the elastomeric tube member 82 may also be covered with elastomeric material 86. In this manner, the portions of the wire members 80 (with or without elastomeric covering 86) which protrude outwardly from the elastomeric tube member 82 may serve to abut against and engage the luminal surfaces of the passageways or blood vessels $BV_1$, $BV_2$, such that body fluid may pass through the lumen 84 of the tube member 82, from one passageway or blood vessel $BV_1$ to the other passageway or blood vessel $BV_2$.

FIGS. 7d–7d' shows another embodiment of a connector apparatus 10k which comprises a continuous segment of wire which is formed into a configuration having four generally U-shaped projections 92 extending laterally outward therefrom in opposite directions.

This apparatus 10k may be utilized as a connector apparatus in and of itself, without any elastomeric covering, such that the U-shaped projection 92 may be placed in abutment with the luminal surfaces of the adjacent passageways or blood vessels $BV_1$, $BV_2$, thereby clipping or holding the openings formed in the passageways or blood vessels $BV_1$, $BV_2$ in alignment with one another, and establishing the desired interconnection of the passageways or blood vessels $BV_1$, $BV_2$.

FIG. 7d' shows an optional elastomeric tube member 94 having the central portion of the wire member formed therein such that the U-shaped projections 92 extend laterally outboard and away from the elastomeric tube member 94. In this manner, the elastomeric tube member is provided with a hollow lumen 96 extending longitudinally therefrom and, when the U-shaped projections are in abutment with the luminal surfaces of the passageways of blood vessels $BV_1$, $BV_2$, the elastomeric tube member 94 will form a discrete conduit or passageway whereby body fluid may pass through the lumen 96 of the tube member 94 from one passageway or blood vessel $BV_1$ to the other passageway or blood vessel $BV_2$.

viii. Sinusoidal Wire Connector Apparatus

FIGS. 8–8a show a connector apparatus 101 which is formed of a wire member 100 which has been formed or bent into multiple sinusoidal waves or convolutions, some of such sinusoidal waves or convolutions being of a first size 102 and others of such sinusoidal waves or convolutions being of a second size 104. Preferably the smaller sinusoidal waves or convolutions 102 are formed in pairs or couplets, with the larger sinusoidal waves or convolutions 104 being also formed in pairs or couplets which are positioned alternately with the pairs or couplets of the smaller sinusoidal waves or convolutions 102. In this manner, when the opposite ends of the wire member 100 are fused or coupled together by way of a sleeve member 101, the smaller sinusoidal waves or convolutions 102 will define a hollow passageway 106 and the larger sinusoidal waves or convolutions 104 may be bent laterally outward from the center of the passageway 106 so as to abut against and engage the respective luminal surfaces of the anatomical passageways or blood vessels $BV_1$, $BV_2$, as shown in FIG. 8a. In this manner, the sinusoidal wire connector apparatus 101 as shown in FIGS. 8, 8a serves to hold the first and second blood vessels $BV_1$, $BV_2$ in connection with one another such that side wall openings formed in such first and second blood vessels $BV_1$ and $BV_2$ will be maintained in direct alignment with one another, thereby allowing body fluid to pass through the passageway 106 of the connector apparatus 101 from the lumen of one blood vessel $BV_1$ to the lumen of the other blood vessel $BV_2$.

It will be appreciated that a covering formed of any suitable material (e.g., elastomeric, fabric, natural graft material, etc.) may be formed on all or part of the device. for example, a tubular covering may be mounted on the mid-portion formed by the smaller sinusoidal waves or convolutions 102 and the basal portions of the larger sinusoidal waves or convolutions 104, and such cover may optionally may extend outwardly over the entireties of the laterally bent portions of the larger sinusoidal waves or convolutions 104, in accordance with the invention as described hereabove in relation to FIGS. 7c and 7d'.

ix. Triplet Coil Type Connector Apparatus

Figure 9:
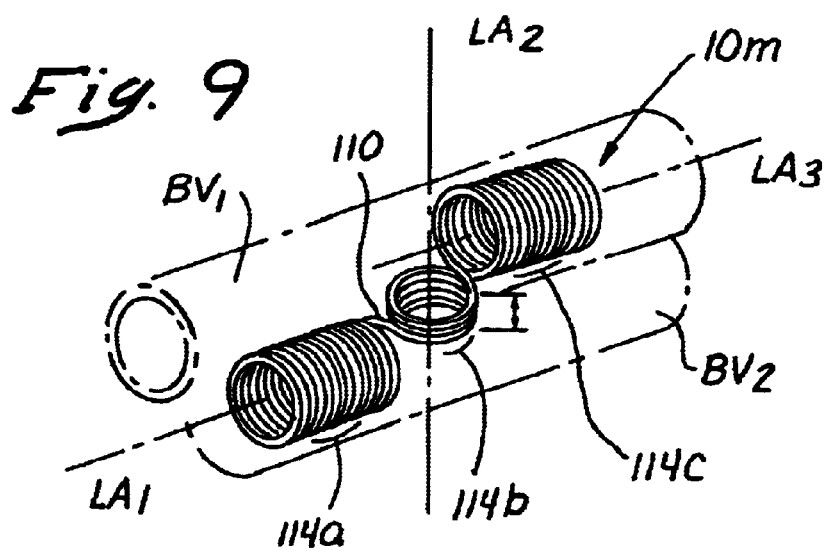
FIG. 9 is a perspective view of a triplet coil type connector apparatus of the present invention, showing the apparatus in a preferred implantation position forming a connection between adjacent tubular anatomical conduits.

FIG. 9 shows a triplet coil type connector apparatus 10m of the present invention comprising a first coil portion 114a, a second coil portion 114b and a third coil portion 114c. The apparatus 10m is formed of a continuous wire member 110 which has been helically wound to form a coil wherein adjacent convolutions of the coil are in direct abutment with one another, or are closely spaced to one another.

The first coil segment 114a has a first longitudinal axis $LA_1$. The coil segment 114b has a second longitudinal axis $LA_2$ which may be perpendicular to the first longitudinal axis $LA_1$ of the first coil segment 114a. The third coil segment 114c has a third longitudinal axis $LA_3$ which may be parallel to the first longitudinal axis $LA_1$ of the first coil segment 114a and perpendicular to the second longitudinal axis $LA_2$ of the first coil segment 114b.

The length 1 of the second coil segment 114b may vary depending upon the desired distance between the first and second passageways or blood vessels $BV_1$, $BV_2$.

The wire member 110 may be formed of any suitable material such as stainless steel, superelastic nickel titanium alloy, etc. The apparatus 10m is preferably sufficiently pliable and resilient such that the three coil segments 114a, 114b, 114c may be disposed in direct alignment with one another about a common longitudinal axis and radially compressed (and concurrently elongated) so as to be positionable within the lumen of a delivery catheter. For most intravascular applications, it will be desirable to compress the entire apparatus 10m to a compact configuration which may be mounted within or upon a delivery catheter of the type referred to in more detail herebelow. Thereafter, the delivery catheter may be advanced through the second blood vessel $BV_2$, through the opening formed between the second blood vessel $BV_2$ and first blood vessel $BV_1$, and into the lumen of the first blood vessel $BV_1$. Thereafter, the third coil segment 114c will be expelled out of the delivery catheter and allowed to assume its radially expanded, operative configuration as shown in FIG. 9.

Thereafter, the delivery catheter will be retracted to a position within or adjacent the opening between the first blood vessel $BV_1$ and second blood vessel $BV_2$, and the second coil segment 114b will be expelled or advanced out of the delivery catheter and allowed to radially expand to its expanded, operative configuration and attitude about the second longitudinal axis $LA_2$ as shown in FIG. 9. Thereafter, the delivery catheter is further retracted into the lumen of the second blood vessel $BV_2$ and the first coil segment 114a is expelled or advanced out of the delivery catheter and allowed to expand to its expanded, operative configuration as shown in FIG. 9.

In this manner, the first and third coil segments 114a, 114c will seat against and frictionally engage the luminal surfaces of the first and second blood vessels $BV_1$ and $BV_2$, respectively, and the second coil segment 114b will traverse any space which exists between the first and second blood vessels $BV_1$ and $BV_2$. It will be appreciated that a tubular covering or enclosure may be formed upon the inner and/or outer surfaces of any and/or all of the coil members 114a, 114b, 114c to provide a flow conduit which is impermeable to fluid, or to enhance the biocompatibility of the apparatus 10m.

x. Flanged Tube Type Connector Apparatus

Figure 10:
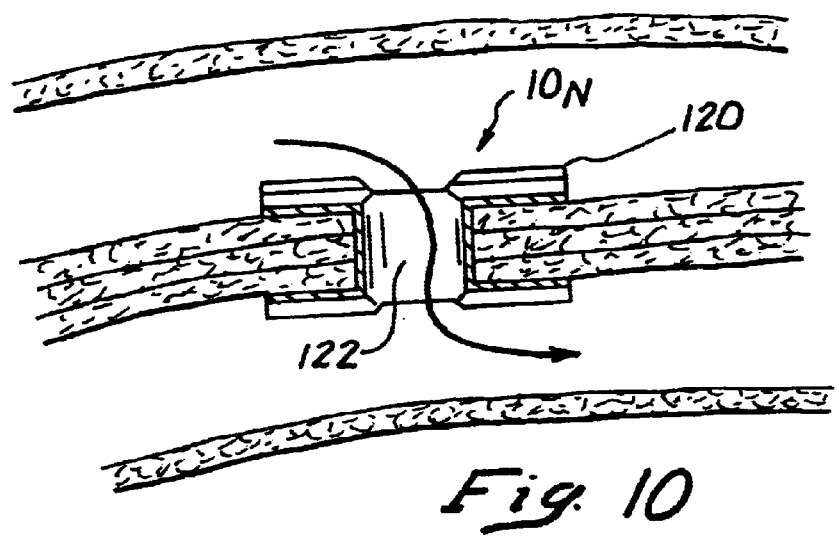
FIG. 10 is a longitudinal sectional view of a flanged tube connector of the present invention in a preferred implantation position forming a connection between adjacent tubular anatomical conduits.
Figure 10A:
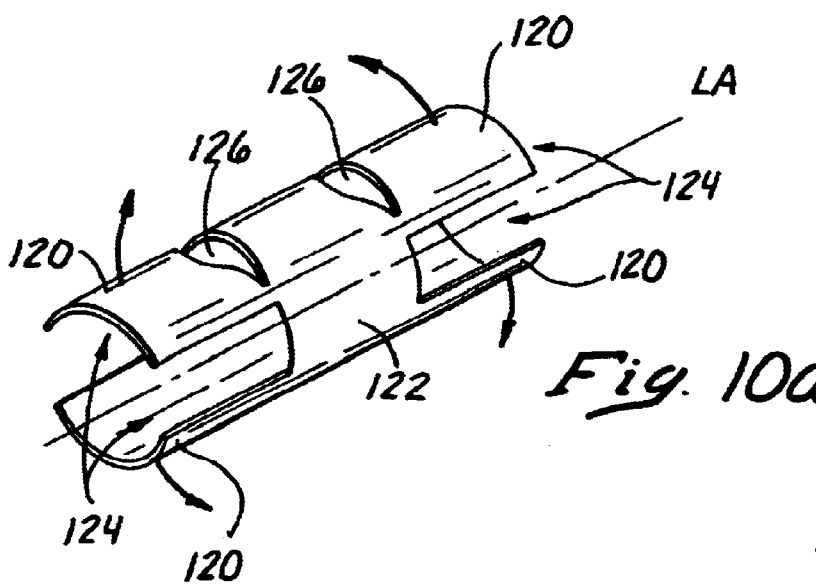
FIG. 10a is a perspective view of a segment of tubing which has been precut for fabrication into the flanged tubular connector apparatus of FIG. 10.
Figure 10B:
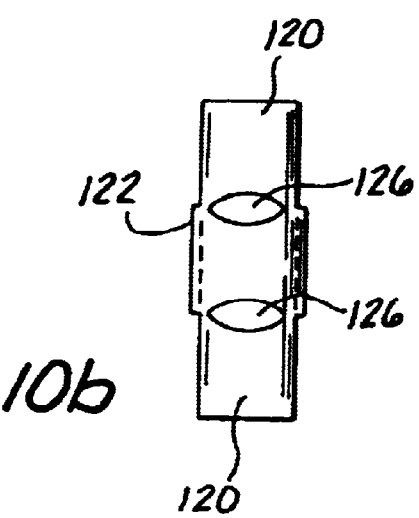

FIGS. 10–10b show a flanged tube type connector apparatus 10n of the present invention. It will be appreciated that, in addition to the specific flang configurations shown in the drawings, such flanges may be formed in many different configurations and designs and/or may include notches, geometries and configurational attributes designed to enhance the ability of the connector apparatus to withstand longitudinal contractions/expansions and rotational/orientation motions of the surrounding tissue.

The embodiment 10n shown in FIG. 10 comprises a segment of tubing which has been notched and formed such that semi-cylindrical or arcuate flanges 120 extend laterally outward from opposite sides of either end of a cylindrical or tubular mid-portion 122. When implanted between two blood vessels, as illustrated in FIG. 10, the semi-cylindrical or arcuate flanges will abut against the luminal surfaces of the blood vessels and will approximate the semi-cylindrical or arcuate shape of the adjacent luminal blood vessel surface. The tubular or cylindrical mid-portion 22 forms a discrete tubular conduit which extends between the opening formed in the adjacent blood vessels, thereby providing a substantially fluid tight conduit through which blood or other bodily fluid may pass.

FIGS. 10–10b illustrate a preferred method of manufacturing this flanged tube type connector apparatus 10n. With reference to FIG. 10a, a segment of cylindrical tubing formed of resilient metal, resilient plastic, shape memory alloy or other suitable material is precut such that two (2) longitudinal notches 124 (e.g., rectangular notches) are formed in each end of the tube, at locations directly opposite one another, as shown. Thereafter, two transverse notches 126 (e.g., arcuate or wedge shaped notches) are formed on either side of the tube such that the center of each such transverse notch 126 is approximately 90° from the centers of the adjacent longitudinal notches 124 formed on that end of the tube. Thereafter, the protruding end portions of the notched tube are deformed or bent outwardly, as indicated by the arrows on FIG. 10a. This results in the formation of the connector apparatus 10n shown in FIG. 10 comprising the tubular mid-portion 122 having the arcuate or semi-cylindrical flanges 120 which extend laterally outward from each end of the tubular mid-portion 122.

xi. Cylindrical Connectors Having Ribbed Outer Surfaces

Figure 11A:
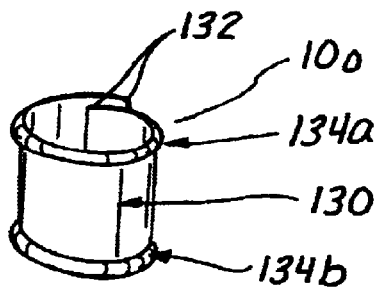
FIG. 11a is a perspective view of a first embodiment of a flanged roll-up connector apparatus of the present invention.
Figure 11B:
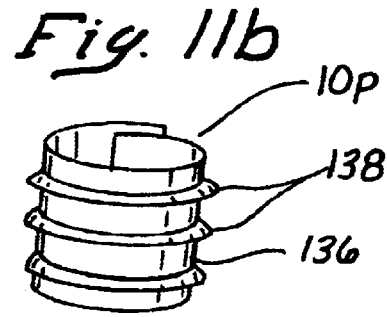
FIG. 11b is a perspective view of a second embodiment of a flanged roll-up connector apparatus of the present invention.
Figure 11C:
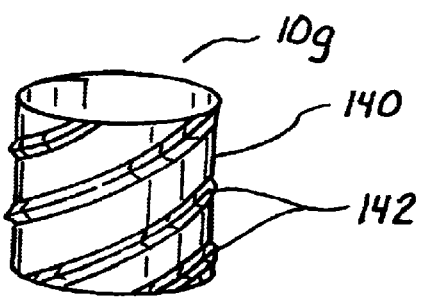
FIG. 11c is a perspective view of a flanged cylindrical connector apparatus of the present invention.

FIGS. 11a–11c show three embodiments of externally ribbed cylindrical connectors 10o, 10p, 10q of the present invention.

The connector 10o shown in FIG. 11a comprises a cylindrical or tubular body 130 formed of a rolled sheet of resilient metal or plastic having overlapping ends 132 such that the rolled cylindrical body may be radially compressed to a radially compact diameter, and will subsequently resiliently return to a radially expanded diameter as shown in FIG. 11a. Cylindrical flanges or ribs 134 are formed about either end of the rolled tube 130, as shown. In this manner, the apparatus 10o may be held in its radially compact state within an introducer or catheter and delivered into a passageway formed between two anatomical structures, where it is allowed to radially expand to its operative configuration. Such radial expansion will cause the flange 134 at one end of the rolled cylindrical body 130 to abut against and engage the luminal surface of a first blood vessel or anatomical structure, surrounding a first opening formed in that blood vessel or anatomical structure. Similarly, the flange or rib 134b at the opposite end of the rolled tubular body 130 will abut against and engage the luminal surface surrounding an opening formed in a second blood vessel or other anatomical structure.

FIG. 11b shows another ribbed connector apparatus 10p which also comprises a rolled cylindrical body portion 136 formed and configured the same as that shown in FIG. 11a. In this apparatus 10p, a plurality of annular flanges or ribs 138 are formed about the outer surface of the rolled cylindrical body 136. When this apparatus 10p is delivered into a passageway between two blood vessels or other anatomical structures and allowed to expand, the flanges or ribs 138 on the outer surface of the rolled cylindrical body will embed into or engage interstitial tissue which surrounds the cylindrical body 136, thereby holding the apparatus 10p in its desired position between openings formed in adjacent blood vessels or anatomical structures. It will be appreciated that this embodiment of the apparatus 10p will be particularly useful in applications wherein firm interstitial tissue surrounds the passageway which extends between the openings formed in the adjacent blood vessels or anatomical structures. Indeed, this apparatus 10p is devoid of any flanges or projections or surfaces which will abut against or engage the luminal surfaces of the adjacent blood vessels or anatomical structure, and relies instead on the engagement of the ribs or flanges 138 with the interstitial tissue to prevent the apparatus 10p from dislodging or longitudinally moving following implantation.

FIG. 11c shows another example of a ribbed cylindrical connector apparatus 10g comprising a continuous cylindrical tubular body 140 having a helical rib or flange 142 formed about the outer surface thereof. The continuous cylindrical body 140 differs from the rolled cylindrical bodies of the embodiments 10o, 10p shown in FIGS. 11a and 11b in that it does not have overlapping ends and can not be radially compressed in a "roll-up" state. Rather, the cylindrical body 140 of this apparatus 10g is of a continuous cylindrical structure and is formed of resilient or collapsible material that will enable the apparatus 10g to be placed in a radially compact or reduced state for delivery into a passageway formed between openings and adjacent blood vessels or anatomical structures. After the tubular body 140 has been delivered and expanded to its operative configuration as shown in FIG. 11c, the helical outer rib or flange 142 will engage the interstitial tissue surrounding the passageway. As in the embodiment shown in FIG. 11b, this apparatus 10g will be particularly useable in applications wherein the passageway formed between the blood vessels or other anatomical structures has firm surrounding interstitial tissue into which the helical rib or flange 142 may imbed.

xii. Possible Modifications of Embodiments to Accommodate Diagonal Passageways or Connections between Anatomical Structures Other than Blood Vessels FIGS. 12 and 13 are intended to show modifications and alternative applications which may be applicable to all of the connector apparatus shown in FIGS. 1–11.

Figure 12:
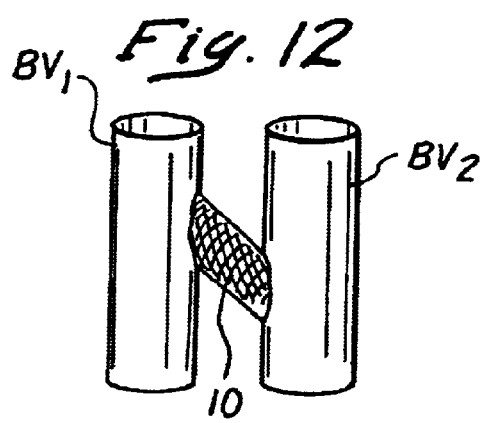
FIG. 12 is a perspective view showing the manner in which any of the connector apparatus of the present invention may be modified to form a non-perpendicular connection between adjacent anatomical structures.

FIG. 12 is illustrative of the concept of forming the ends of each connector apparatus 10 such that the ends are non-perpendicular to the longitudinal axis LA of the apparatus 10. Such angle-cutting of the ends of the connector apparatus 10 will be applicable when the connector apparatus 10 is to be disposed within a diagonal or curved passway formed between openings which are not directly opposite one another on adjacent anatomical structures or blood vessels $BV_1$, $BV_2$. This aspect of the invention will be particular applicable in certain arterial bypass procedures, such as those described in U.S. patent application Ser. Nos. 08/730,327 and 08/730,496, when it is desired to form curved or diagonal blood flow passageways to minimize turbulence and to promote substantially laminar blood flow through the passageway and into the bypass vessel.

Figure 13:
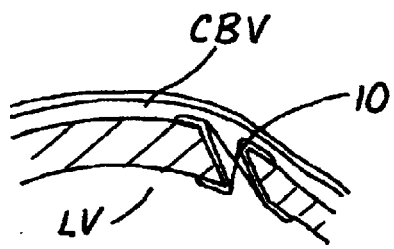
FIG. 13 is a perspective view of a segment of myocardium showing an alternative application of the connector apparatus of the present invention to form a connection between a coronary blood vessel and a chamber of the heart.

FIG. 13 shows a connector apparatus 10, which has the configuration of the specific apparatus 10k shown in FIG. 7d, disposed within a transmyocardial passageway formed between a coronary blood vessel CBV and the left ventricle LV of the heart. In this manner, FIG. 13 serves as an example of an application wherein any or all of the connector apparatus 10 of the present invention may be used to form a connection between anatomical structures other than two blood vessels (i.e., a coronary blood vessel and a chamber of the heart).

xiii. Possible Modification of Embodiments to Accommodate or Conform to Passageways of Differing Length It will be appreciated by those skilled in the art that the length or distance between the first and second anatomical structures may vary considerably. Thus, for embodiments of the connector apparatus 10 which are of fixed length, it may be desirable to manufacture or provide such connector apparatus in a variety of lengths and sizes so as to allow the operator to select the appropriate length or size for use in the instant application. Alternatively, many if not all of the embodiments of the present invention may be constructed such that the connecting portion of the connector apparatus 10 is elastic, adjustable, telescoping, distendable, of according configuration, or otherwise adjustable to accommodate or conform to passageways of differing length.

xiv. Delivery and Implantation of the Connector Apparatus

It should be generally understood that the connector may be delivered via any number or possible delivery mechanisms including but not limited to:

1. Delivery mechanisms which trap the connector initially within an inner tubular member and an outer tubular member wherein movement of the one member relative to the other allows the connector to be exposed and deployed at first partially to allow the first set of engagement members to come in contact with the first lumen and then deployed fully to allow the second set of engagement members to come into contact with the second lumen.
2. Connectors which are mounted onto a balloon, covered or non-covered by a temporary sheath, and then deployed with the assistance or forcibly directed by the balloon to their engaging position.
3. Connectors mounted between two balloons, initially covered or non-covered by a sheath, wherein the balloons act principally to bring the engagement members into contact with the apposing lumens; however, the two balloons may further act to dilate and further deploy the connector within the channel.
4. Two piece connectors, such as the rivet device shown in FIG. 6, may be deployable via two members mounted over a central core capable of moving towards each other such that the resultant force acts to engage the inner aspect of the two rivet components, fixing them in apposition.
5. Delivery mechanisms which hold the connector in a compressed state within a sheath and deploy the connector through the relative movement of an inner push-rod mechanism, allowing it to deploy in a first partially expanded state, and then to a fully expanded state.
6. Delivery of connectors which may be rotationally inserted into the tissue, expanding it as it is advanced into position, and then disengaged, allowing the connector to remain anchored within the channel that was partially enhanced by the delivery mechanism.
7. Delivery mechanisms which utilize some form of thermal, electrical, fluid or chemical means to induce a conformational change in the connector upon proper positioning in the channel.

Examples of suitable delivery catheters for implanting connector apparatus 10 of the present invention are shown in FIGS. 14a–14d.

Figures 14A, 14B, 14C:
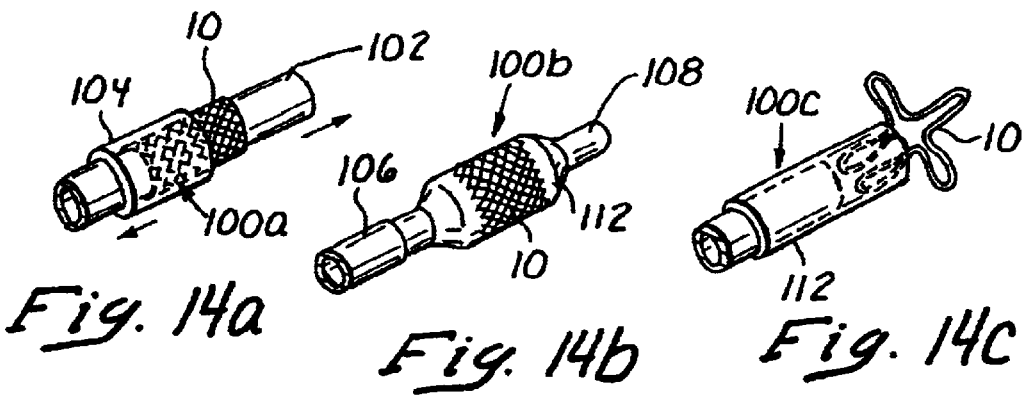
FIG. 14a is a schematic showing of a retractable sheath type delivery catheter useable to deliver connector apparatus of the present invention.
FIG. 14b is a schematic showing of an inflatable balloon type delivery catheter useable to deliver connector apparatus of the present invention.
FIG. 14c is a schematic showing of a push rod type delivery catheter useable to deliver connector apparatus of the present invention.

FIG. 14a shows a withdrawable sheath type delivery catheter 100a comprising an elongate inner member 102 having a connector apparatus 10 of the present invention mounted thereon, and a surrounding retractable outer sheath 104. The connector apparatus 10 in this embodiment is preferably self-expanding or formed of shape memory material which will radially expand when warmed to body temperature. When the sheath 104 is fully advanced over the connector apparatus 10, the sheath will radially constrain and hold the connector apparatus 10 in the desired radially compact configuration. After the catheter 100a has been advanced to the desired location, the sheath 104 may then be retracted (or alternatively the inner member 102 may be advanced) thereby removing the surrounding constraint from the connector apparatus 10 such that the connector apparatus 10 may radially expand and become implanted in the desired location.

FIG. 14b shows a balloon delivery catheter 100b comprising a tubular catheter body 106 and an elongate member 108 having an inflatable balloon 110 formed thereon. The connector apparatus 10 is initially mounted on the deflated balloon 110 with the connector apparatus 10 in its radially compact configuration. After the catheter 100b has been advanced to the desired implantation site, the catheter 106 is withdrawn (or the inner member 108 is advanced) and the balloon in inflated so as to radially expand the connector apparatus 10 and to cause the connector apparatus to become implanted at its desired implantation site.

FIG. 14c shows a push rod type delivery catheter 100c comprising an outer tubular sheath 112 an advanceable push rod 114. The connector apparatus 10 is initially placed in the lumen of the catheter sheath 112, ahead of the distal end of the push rod 114, with the connector apparatus 10 in its radially compact configuration. After the catheter 100c has been advanced to the desired implantation site the catheter 112 may be retracted (or the push rod 114 may be advanced) to expel the connector apparatus 10 out of the distal end of the catheter. In this manner, the connector apparatus 10 is relieved of any surrounding constraint and is permitted to radially expand and become implanted in the desired implantation site. It will be appreciated that this embodiment is particularly suitable for self-expanding embodiments of the connector apparatus 10 or those formed of shape memory material which will expand upon warming to body temperature. A more detailed description of this push rod type of delivery catheter is set forth in parent application Ser. No. 08/730,327, filed on Oct. 11, 1996.

Figures 14D, 14E:
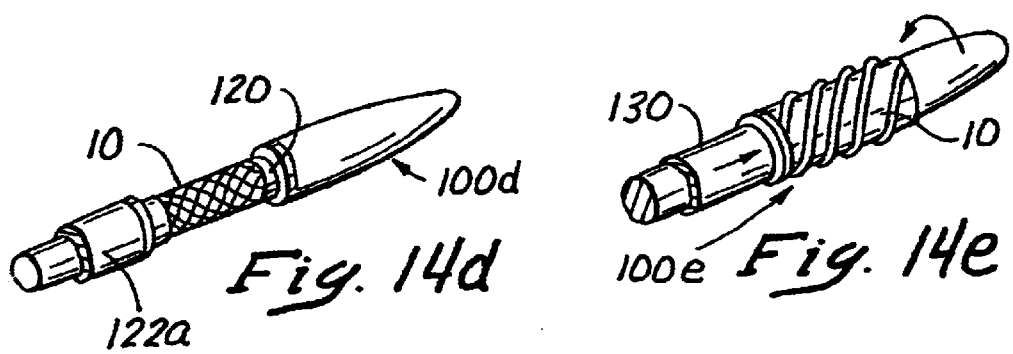
FIG. 14d is a schematic showing of an alter-apposing slider sheath type delivery catheter useable to deliver connector apparatus of the present invention.
FIG. 14e is a schematic showing of a rotatable delivery catheter useable to deliver and implant connector apparatus of the present invention.

FIG. 14d shows a slider sheath type delivery 100d. This device comprises an inner member 120 upon which the connector apparatus 10 is mounted in its radially compact configuration. Proximal and distal sheaths 122a 122b are initially drawn together such that the distal end of the proximal sheath member 122a is in abutment with the proximal end of the distal sheath member 122b, thereby covering and providing an enclosure or constraint about the radially collapsed connector apparatus 10. After the catheter 100b has been advanced to the desired implantation site, one or both of the proximal and distal sheath member 122a, 122b is/are moved away from the other so as to expose the radially compact connector apparatus 10, as shown in FIG. 14b. In embodiments where the connector apparatus 10 is self-expanding or formed of shape memory material which will expand upon warming to body temperature, such opening of the slider sheaths 122a, 122b will allow the connector apparatus 10 to expand and become implanted at its desired implantation site. In other embodiments wherein the connector apparatus 10 is formed of plastically deformable material, the radial expansion member such as an inflatable balloon will be mounted on the inner member 120 beneath the radially compact connector apparatus 10. Such radial expansion or balloon may then be radially expanded (e.g., inflated) to radially expand and plastically deform the connector apparatus 10, as desired.

FIG. 14e shows a rotatable delivery catheter 100e which comprises an elongate member 130 which is in itself rotatable, or which is provided with a rotatable distal portion. The connector apparatus 10 is mounted upon the distal portion of the elongate member 130, as shown. After the elongate member 130 has been advanced to a position adjacent the desired implantation site, the elongate member 130 or the distal portion thereof is rotated, and the elongate member 130 is further advanced so as to rotatably drive and advance the connector apparatus 10 into the desired implantation site. It will be appreciated that this embodiment is particularly useable for connector apparatus 10 which are not radially expandable, and or those having helical or spiral ribs on the outer surface thereof (e.g., FIG. 11c) and/or for those having a leading edge which is sharpened or otherwise adapted to cut tissue so as to bore and form or enlarge the passageway as the connector apparatus is advanced.

Figure 15A:
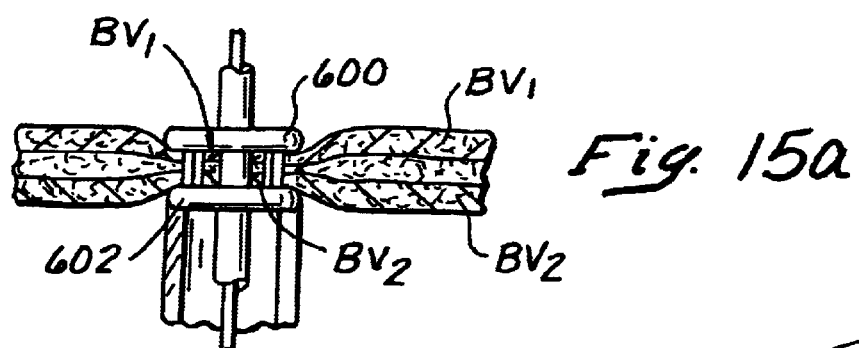
FIG. 15a is a showing of a two-piece connector apparatus as described and claimed in parent application Ser. No. 08/730,327, modified to illustrate the manner in which the connecting portion of the connector apparatus may protrude through tissue and lay outside of the passageway which has been formed between the adjacent anatomical structures.
Figure 15A:
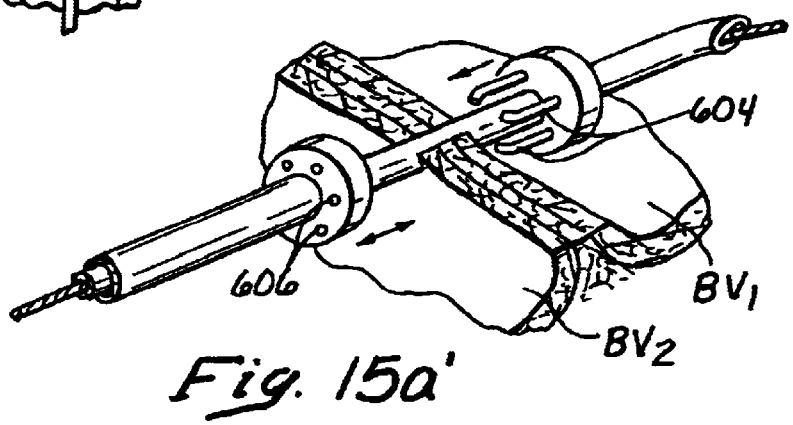

These additional connector delivery catheters shown in FIGS. 14a–14e are examples of the types of delivery catheter devices which may be utilized, in addition to the double balloon catheter shown in FIGS. 3''', 4''' and 5'', and described more fully hereabove.

xv. Connector Apparatus which Include Tissue Puncturing Connecting Portions Such that the Connecting Portions May Reside Outside of the Fluid Flow Passageway FIGS. 15a–15a' show a modified rivet type connector apparatus 10e''', of the type previously described and claimed in U.S. patent application Ser. No. 08/730,327. This connector apparatus 10e''' comprises first and second annular engagement members 600, 602, and a plurality of connecting members 604 which extend from first engagement member 600 and which are adapted to engage and connect to receiving aperture 606 formed in the second engagement member 602. As shown in FIGS. 9a and 9a', the connector member 604 may be capable of penetrating through the tissue, and may be situated such that they will pass through the walls of the first and second blood vessels $BV_1$, $BV_2$ and through any intervening interstitial tissue such that the connector members 604 will lay outside of the previously formed passageway or channel, and outside of the openings formed in the respective first and second blood vessels $BV_1$, $BV_2$.

These drawings illustrate that the connector portion of the connector apparatus 10 need not extend through or reside within the fluid flow passageway, but actually may protrude through intervening tissue and reside outboard of the passageway, as shown.

These delivery devices are generally capable of being advanced over a guide wire into the channel and may assist passively or actively in the proper deployment of the connector. Further it should be understood that various radiopaque or imageable markers may be placed in important locations on the delivery mechanism to permit proper placement or monitoring of placement during deployment. Further, it is also possible that various recapturing mechanisms such as thread(s), hood(s) or other capturing or securing means may be provided to allow for the reversible deployment of the connector in the instance where it was found to be improperly placed.

The invention has been described hereabove with reference to certain presently preferred embodiments only, and no effort has been made to exhaustively describe and show all possible embodiments in which the invention may take physical form. Indeed, numerous alterations, modifications and changes may be made to the above-described embodiments without departing from the spirit and scope of the invention. For example, specific elements or attributes of one embodiment may be incorporated into any or all of the other embodiments shown in the drawings, and may be interchanged or recombined in any possible combinations, and all such modifications and combinations of the elements and components of the invention described herein are intended to be within the scope of the following claims.

What is claimed is:

1. An apparatus for connecting a first opening formed in a first anatomical structure to a second opening formed in a second anatomical structure, said first anatomical structure having a wall and an inner space defined at least in part by an inner surface of the first anatomical structure's wall and said second anatomical structure having a wall and an inner space defined at least in part by an inner surface of the second anatomical structure's wall, said apparatus being initially disposable in radially collapsed configuration wherein it may be transluminally delivered to an intended implantation site and subsequently transitionable to a radially expanded configuration, said apparatus being formed of plastic and, when implanted in its radially expanded configuration, comprising:
    a) a first engagement portion which engages the wall of the first anatomical structure adjacent to the perimeter of the first opening formed therein;
    b) a second engagement portion which engages the wall of the second anatomical structure adjacent to the perimeter of the second opening formed therein; and,
    c) a tube connecting the first engagement portion to the second engagement portion, said tube being configured to define a flow channel through which fluid may flow from the inner space of the first anatomical structure, through the first opening, through the second opening and into the inner space of the second anatomical structure, wherein said first and second engagement portions comprise projections extending laterally outward from opposite ends of the tube.

2. The apparatus of claim 1 wherein said tube comprises a frame which will maintain an open passageway through surrounding tissue.

3. The apparatus of claim 1 wherein said tube is a mesh tube.

4. The apparatus of claim 1 wherein the projection of said second engagement member is a splayable member initially maintained in a non-splayed configuration and, after being positioned adjacent the second opening formed in the second anatomical structure, is convertible to a splayed configuration wherein the projection engages the inner wall of the second anatomical structure adjacent the second opening formed therein.

5. The apparatus of claim 4 wherein the projection of said first engagement member is self-splaying and resiliently biased to its splayed configuration.

6. The apparatus of claim 1 wherein said apparatus is initially deployable in a radially compact configuration, said apparatus being subsequently radially expandable to an operative configuration wherein at least said first and second engagement portions will abut against and engage the adjacent surfaces of the first and second anatomical structures.

7. The apparatus of claim 6 wherein said apparatus is self-expanding and resiliently biased to its operative configuration.

8. The apparatus of claim 6 wherein said apparatus is plastically formable and is initially formed in its radially compact configuration, and is subsequently deformable to its operative configuration by exertion of radial pressure upon said apparatus.

9. The apparatus of claim 1 wherein said apparatus is a hyperboloidal helical coil.

10. The apparatus of claim 9 wherein said hyperboloidal helical coil is formed of a multiplicity of adjacent convolutions of wire, and wherein at least some of said adjacent convolutions are fused to one another.

11. The apparatus of claim 1 wherein said first and second engagement portions comprise frusto-conical helical coils having outer and inner ends, the outer ends of said helical coils being larger in diameter than the inner ends thereof.

12. The apparatus of claim 1 wherein said tube has inwardly arched side walls such that the ends of the tube are of larger diameter than the middle of the tube.

13. The apparatus of claim 12 wherein said tube is a solid tube.

14. The apparatus of claim 12 wherein said tube is mesh tube.

15. The apparatus of claim 12 wherein said tube is formed of a material selected from the group of materials consisting of:
    a helical wire coil;
    a helical filament coil;
    wire mesh;
    a shape memory alloy;
    plastic;
    metal;
    woven fabric;
    elastic material; and,
    elastomeric material.

16. The apparatus of claim 12 wherein at least one of the projections is splayable.

17. The apparatus of claim 16 wherein the at least one splayable projection is self-splaying and resiliently biased to an outwardly splayed configuration.

18. The apparatus of claim 16 wherein the at least one splayable projection is plastically deformable, and initially formed in a non-splayed configuration but subsequently deformable by exertion of outwardly directed pressure thereagainst.

19. The apparatus of claim 1 wherein said connector apparatus is a flanged tube connector wherein said connecting portion comprises a tube, and wherein said first and second engagement portions comprise semi-cylindrically shaped flanges which extend laterally outward from opposite ends of the said tube.

20. The apparatus of claim 19 wherein said flanged tube connector is formed by a method comprising the steps of:
    a) providing a tube having a longitudinal axis, a cylindrical side wall disposed about said longitudinal axis, first and second ends, and a hollow lumen extending longitudinally therethrough;
    b) forming first and second rectangular notches at directly opposite locations in the first end of said tube, said rectangular notches having side edges which are parallel to said longitudinal axis, and an end which is perpendicular to said longitudinal axis;
    c) forming third and fourth rectangular notches at directly opposite locations in the second end of said tube, said rectangular notches having side edges which are parallel to said longitudinal axis, and an end which is perpendicular to said longitudinal axis;

d) forming first and second generally arcuate notches at directly opposite locations in the cylindrical side wall of the tube, in alignment with the ends of the first and second rectangular notches;

e) forming third and fourth generally arcuate notches at directly opposite locations in the cylindrical side wall of the tube, in alignment with the ends of the third and fourth rectangular notches; and, f) outwardly bending the remaining cylindrical side walls of the tube adjacent said rectangular notches such that said generally arcuate notches become substantially closed, and said outwardly bent portions of the side wall form semi-cylindrical flanges which protrude outwardly from opposite ends of the remaining mid-portion of the tube, generally perpendicular to said longitudinal axis.

21. The apparatus of claim 1 wherein said tube is configured to extend through and reside within a passageway formed between said first and second openings.

22. The apparatus of claim 1 wherein said tube is constructed to penetrate through tissue and is positioned to reside within surrounding tissue and outboard of a passageway which has been formed between the first and second openings.

23. The apparatus of claim 1 wherein said apparatus is adapted to transmit energy to tissue with which the apparatus comes into contact, thereby providing an energy-mediated treatment to said tissue.

24. The apparatus of claim 1 wherein said first and second engagement portions comprise annular members, and wherein said connecting portion comprises:

at least one connector member formed on said first engagement portion and adapted to insert into an engaged said second engagement portion when said first and second engagement portions are moved toward one another.

25. The apparatus of claim 24 wherein said connector portion comprises at least one elongate member.

26. The connector apparatus of claim 1 wherein said apparatus further comprises at least one magnet to facilitate connection of the first engagement portion to the second engagement portion.

27. The connector apparatus of claim 1 wherein said tube comprises scaffolding to deter ingrowth into the flow channel formed between the first and second anatomical structures.

28. The connector apparatus of claim 1 wherein said connector apparatus has a leading edge adapted to sever tissue as said connector apparatus is advanced.

29. The connector apparatus of claim 1 wherein said connector apparatus has an outer covering which is selected from the group of outer coverings consisting of:

a synthetic tube graft;

a natural tube graft;

a chemical coating;

an antithrombogenic coating; and, an antimicrobial coating.

30. The connector apparatus of claim 1 wherein said connector apparatus further comprises at least one radioactive material to deter tissue ingrowth following implantation.

31. The connector apparatus of claim 1 wherein said connecting portion includes adjusting structure adapted to pull said first and second engagement portions toward one another.

32. The connector apparatus of claim 31 wherein said adjusting structure enables the connector apparatus to form connections between anatomical structures which are separated by varying distances, and is selected from the group consisting of:

telescoping structure and distendable structure.

33. The connector apparatus of claim 31 wherein said adjusting structure is elastic, and serves to minimize the length of the channel wherein the connector apparatus is implanted.

34. The apparatus of claim 1 wherein the projection of said first engagement portion is a splayable member which is initially maintained in a non-splayed configuration and, after being positioned adjacent the first opening formed in the first anatomical structure, is convertible to a splayed configuration wherein said first engagement member engages the inner wall of the first anatomical structure adjacent the first opening.

35. The apparatus of claim 34 wherein the projection of said first engagement member is self-splaying and resiliently biased to its splayed configuration.

36. The apparatus of claim 34 wherein the projection of said first engagement portion is plastically deformable and is initially formed in its non-splayed configuration, and is subsequently deformable to its splayed configuration by exertion of pressure against said engagement member.

37. An apparatus for connecting a first opening formed in a first anatomical structure to a second opening formed in a second anatomical structure, said first anatomical structure having a wall and an inner space defined at least in part by an inner surface of the first anatomical structure's wall and said second anatomical structure having a wall and an inner space defined at least in part by an inner surface of the second anatomical structure's wall, said apparatus being initially disposable in radially collapsed configuration wherein it may be transluminally delivered to an intended implantation site and subsequently transitionable to a radially expanded configuration, said apparatus comprising an elongate wire member having a series of sinusoidal bends formed therein, and first and second ends, the first and second ends of said wire member being joined to one another to form a ring wherein, when said apparatus is implanted in its radially expanded configuration:

a) a first portion of at least some of said sinusoidal bends turns outwardly to form projections engaging the wall of the first anatomical structure adjacent to the perimeter of the first opening formed therein;

b) a second portion of at least some of said sinusoidal bends turns outwardly to form projections engaging the wall of the second anatomical structure adjacent to the perimeter of the second opening formed therein; and c) the ring defines a flow channel through which fluid may flow from the inner space of the first anatomical structure, through the first opening, through the second opening and into the inner space of the second anatomical structure;

wherein at least one of the first and second portions is configured to self-expand from a radially constrained, non-splayed initial configuration to a splayed configuration such that the projections engage the wall of the first or second anatomical structure after being positioned adjacent the first or second opening and relieved of radial restraint.

38. The apparatus of claim 37, wherein said sinusoidal bends include a plurality of first sinusoidal bends of a first amplitude, and a plurality of second sinusoidal bends of a second amplitude, said second amplitude being larger than said first amplitude, said second sinusoidal bends of said second amplitude being bent outwardly to form said projections, and said first sinusoidal bends of said first amplitude remaining without outward bending so as to form said ring.

39. The apparatus of claim 37 wherein said ring is configured to extend through and reside within a passageway formed between said first and second openings.

40. The apparatus of claim 37 wherein said ring is constructed to penetrate through tissue and is positioned to reside within surrounding tissue and outboard of a passageway formed between said first and second openings.

41. The apparatus of claim 37 wherein said apparatus is adapted to transmit energy to tissue with which the apparatus comes into contact, thereby providing an energy mediated treatment to said tissue.

42. The apparatus of claim 37 wherein said apparatus comprises scaffolding to deter ingrowth into the flow channel formed between the first and second anatomical structures.

43. The apparatus of claim 37 wherein said apparatus has a leading edge, and wherein said leading edge is adapted to sever tissue as said apparatus is advanced.

44. The apparatus of claim 37 wherein said apparatus has an outer covering which is selected from the group of outer coverings consisting of:
  a synthetic tube graft;
  a natural tube graft;
  a chemical coating;
  an anti-thrombogenic coating; and
  an anti-microbial coating.

45. The apparatus of claim 37 wherein said apparatus further comprises at least one radioactive material to deter tissue ingrowth following implantation.

46. An apparatus for connecting a first opening formed in a first anatomical structure to a second opening formed in a second anatomical structure, said first anatomical structure having a wall and an inner space defined at least in part by an inner surface of the first anatomical structure's wall, and said anatomical structure having a wall and an inner space defined at least in part by an inner surface of the second anatomical structure's wall, said apparatus being initially disposable in a radially collapsed configuration wherein it may be transluminally delivered to an intended implantation site and subsequently transitionable to a radially expanded configuration, said apparatus when implanted in its radially expanded configuration comprising:
  a) a first engagement portion which engages the wall of the first anatomical structure adjacent to the perimeter of the first opening formed therein;
  b) a second engagement portion which engages the wall of the second anatomical structure adjacent to the perimeter of the second opening formed therein;
  c) a connecting portion connecting the first engagement portion to the second engagement portion, said connecting portion being configured to define a flow channel through which fluid may flow from the inner space of the first anatomical structure, through the first opening, through the second opening and into the inner space of the second anatomical structure; and
  d) a leading edge adapted to sever tissue as said apparatus is advanced.

47. The apparatus of claim 46 wherein said connecting portion is a tubular member.

48. The apparatus of claim 46 wherein said connecting portion is a wire member.

49. The apparatus of claim 46 wherein said connecting portion comprises a frame which will maintain an open passageway through surrounding tissue.

50. The apparatus of claim 46 wherein said connecting portion is a mesh tube.

51. The apparatus of claim 46 wherein said first engagement portion is a splayable member which is initially maintained in a non-splayed configuration and, after being positioned adjacent the first opening formed in the first anatomical structure, is convertible to a splayed configuration wherein said first engagement member will engage the inner wall of the first anatomical structure adjacent the first opening formed therein.

52. The apparatus of claim 51 wherein said first engagement member is self-splaying and resiliently biased to its splayed configuration.

53. The apparatus of claim 51 wherein said first engagement portion is plastically deformable and is initially formed in its non-splayed configuration, and is subsequently deformable to its splayed configuration by exertion of pressure against said engagement member.

54. The apparatus of claim 46 wherein said second engagement portion is a splayable member which is initially maintained in a non-splayed configuration and, after being positioned adjacent the second opening formed in the second anatomical structure, is convertible to a splayed configuration wherein said second engagement member will engage the inner wall of the second anatomical structure adjacent the second opening formed therein.

55. The apparatus of claim 54 wherein said second engagement member is self-splaying and resiliently biased to its splayed configuration.

56. The apparatus of claim 54 wherein said second engagement portion is plastically deformable and is initially formed in its non-splayed configuration, and is subsequently deformable to its splayed configuration by exertion of pressure against said engagement member.

57. The apparatus of claim 46 wherein said apparatus is initially deployable in a radially compact configuration, said apparatus being subsequently radially expandable to an operative configuration wherein at least said first and second engagement portions will abut against and engage the adjacent surfaces of the first and second anatomical structures.

58. The apparatus of claim 57 wherein said apparatus is self-expanding and resiliently biased to its operative configuration.

59. The apparatus of claim 57 wherein said apparatus is plastically deformable and is initially formed in its radially compact configuration, and is subsequently deformable to its operative configuration by exertion of radial pressure upon said apparatus.

60. The apparatus of claim 46 wherein said apparatus is a hyperboloidal helical coil.

61. The apparatus of claim 60 wherein said hyperboloidal helical coil is formed of a multiplicity of adjacent convolutions of wire, and wherein at least some of said adjacent convolutions are fused to one another.

62. The apparatus of claim 46 wherein said first and second engagement portions comprise frusto-conical helical coils having outer and inner ends, the outer ends of said helical coils being larger in diameter than the inner ends thereof.

63. The apparatus of claim 62 wherein said connecting portion of said apparatus comprises a tubular member mounted between and connecting the inner ends of said frusto-conical helical coils.

64. The apparatus of claim 46 wherein said apparatus is a tube having inwardly arched side walls such that the ends of the tube are of larger diameter than the middle of the tube, said ends of the tube thereby forming said first and second engagement portions, and said middle of the tube thereby forming said connecting portion.

65. The apparatus of claim 64 further comprising at least one splayable engagement member formed on each end of the tube.

66. The apparatus of claim 65 wherein said at least one splayable engagement member is self-splaying and resiliently biased to an outwardly splayed configuration.

67. The apparatus of claim 65 wherein said at least one engagement member is plastically deformable, and initially formed in a non-splayed configuration but subsequently deformable by exertion of outwardly directed pressure thereagainst.

68. The apparatus of claim 64 wherein said tube is a solid tube.

69. The apparatus of claim 64 wherein said tube is a mesh tube.

70. The apparatus of claim 64 wherein said tube is formed of a material selected from the group of materials consisting of:
a helical wire coil;
a helical filament coil;
wire mesh;
a shape memory alloy;
plastic;
metal;
woven fabric;
elastic material; and
elastomeric material.

71. The apparatus of claim 46 wherein said apparatus comprises a plastic structure wherein the connecting portion comprises a tube, and wherein the first and second engagement portions comprise projections which extend laterally outwardly from opposite ends of said tube.

72. The apparatus of claim 46 wherein said apparatus comprises a wire clip, wherein said first and second engagement portions comprise wire projections which extend laterally outward form the center of the clip, and wherein said connecting portion comprises traversing segments of wire which extend between said projections.

73. The apparatus of claim 46 wherein said apparatus comprises an elongate wire member having a series of generally sinusoidal bends formed therein, and first and second ends, the first and second ends of said wire member being joined to one another to form a ring, and at least some of said sinusoidal bends being turned outwardly therefrom to form projections which extend outwardly from said ring, said projections thereby forming said first and second engagement portions, and said ring thereby forming said connecting portion.

74. The apparatus of claim 73 wherein said sinusoidal bends include a plurality of first sinusoidal bends of a first amplitude,and a plurality of second sinusoidal bends of a second amplitude, said second amplitude being larger than said first amplitude, said second sinusoidal bends of said second amplitude being bent outwardly to form said projections, and said first sinusoidal bends of said first amplitude remaining without outward bending so as to form said ring.

75. The apparatus of claim 46 wherein said apparatus comprises a triplet coil connector comprising:
a first helical coil having a first longitudinal axis, a second helical coil having a second longitudinal axis which is not parallel to the first longitudinal axis, and a third helical coil having a third longitudinal axis, said third longitudinal axis being perpendicular to said second longitudinal axis but spaced apart from said first longitudinal axis;
said triplet coil connector being thereby implantable within the body such that the first helical coil is within the inner space of the first anatomical structure, said third helical coil is within the inner space of the second anatomical structure, and said second helical coil extends between said first and second openings in said first and second anatomical structures.

76. The apparatus of claim 75 wherein said first, second, and third coil members are formed of helically wound wire.

77. The apparatus of claim 75 wherein said first, second, and third coil members are formed of helically wound filament.

78. The apparatus of claim 46 wherein said connecting portion comprises a tube, and wherein said first and second engagement portions comprises semi-cylindrically shaped flanges which extend laterally outward from opposite ends of said tube.

79. The apparatus of claim 78 wherein said flanged tube connector is formed by a method comprising the steps of:
a) providing a tube having a longitudinal axis, a cylindrical side wall disposed about said longitudinal axis, first and second ends, and a hollow lumen extending longitudinally therethrough;
b) forming first and second rectangular notches at directly opposite locations in the first end of said tube, said rectangular notches having side edges which are parallel to said longitudinal axis, and an end which is perpendicular to said longitudinal axis;
c) forming third and fourth rectangular notches at directly opposite locations in the second end of said tube, said rectangular notched having side edges which are parallel to said longitudinal axis, and an end which is perpendicular to said longitudinal axis;
d) forming first and second generally arcuate notches at directly opposite locations in the cylindrical side wall of the tube, in alignment with the ends of the first and second rectangular notches;
e) forming third and fourth generally arcuate notches at directly opposite locations in the cylindrical side wall of the tube, in alignment with the ends of the third and fourth rectangular notches; and
f) outwardly bending the remaining cylindrical side walls of the tube adjacent said rectangular notches such that said generally arcuate notches become substantially closed, and said outwardly bent portions of the side wall form semi-cylindrical flanges which protrude outwardly from opposite ends of the remaining midportion of the tube, generally perpendicular to said longitudinal axis.

80. The apparatus of claim 46 wherein said connecting portion is configured to extend through and reside within a passageway formed between said first and second openings.

81. The apparatus of claim 46 wherein said tube is constructed to penetrate through tissue and is positioned to reside within surrounding tissue and outboard of a passageway which has been formed between the first and second openings.

82. The apparatus of claim 46 wherein said apparatus is adapted to transmit energy to tissue with which the apparatus is adapted to transmit energy to tissue with which the apparatus comes into contact, thereby providing an energy-mediated treatment to said tissue.

83. The apparatus of claim 46 wherein said first and second engagement portions comprise annular members, and wherein said connecting portion comprises:

at least one connector member formed on said first engagement portion and adapted to insert into said second engagement portion when said first and second engagement portions are moved toward one another.

84. The apparatus of claim 83 wherein said connecting portion comprises at least one elongate member.

85. The apparatus of claim 46 wherein said apparatus further comprises at least one magnet to facilitate connection of the first engagement portion to the second engagement portion.

86. The apparatus of claim 46 wherein said connecting portion comprises scaffolding to deter ingrowth into the flow channel formed between the first and second anatomical structures.

87. The apparatus of claim 46 wherein said apparatus has an outer covering which is selected from the group of outer coverings consisting of:

a synthetic tube graft;

a natural tube graft;

a chemical coating;

an antithrombogenic coating; and, an antimicrobial coating.

88. The apparatus of claim 46 wherein said connector apparatus further comprises at least one radioactive material to deter tissue ingrowth following implantation.

89. The apparatus of claim 46 wherein said connecting portion is constructed to pull said first and second engagement portions toward one another.

90. The apparatus of claim 89 wherein said pulling of the first and second engagement members toward one another enables the connector apparatus to form connection between anatomical structures which are separated by varying distances.

91. The apparatus of claim 89 wherein said pulling of the first and second engagement members toward one another serves to minimize the length of the channel wherein the connector apparatus is implanted.

\* \* \* \* \*